United States Patent [19]

Takehana et al.

[11] Patent Number: 4,884,557
[45] Date of Patent: Dec. 5, 1989

[54] ENDOSCOPE FOR AUTOMATICALLY ADJUSTING AN ANGLE WITH A SHAPE MEMORY ALLOY

[75] Inventors: Sakae Takehana; Yasuhiro Ueda; Tomohisa Sakurai, all of Tokyo, Japan

[73] Assignee: Olympus Optical Co., Ltd., Tokyo, Japan

[21] Appl. No.: 193,294

[22] Filed: May 11, 1988

[30] Foreign Application Priority Data

| May 15, 1987 | [JP] | Japan | 62-118308 |
| May 25, 1987 | [JP] | Japan | 62-127721 |
| Aug. 5, 1987 | [JP] | Japan | 62-194300 |
| Sep. 11, 1987 | [JP] | Japan | 62-227585 |
| Oct. 8, 1987 | [JP] | Japan | 62-254171 |
| Apr. 12, 1988 | [JP] | Japan | 63-91091 |

[51] Int. Cl.$^4$ .............................................. A61B 1/00
[52] U.S. Cl. ........................................ 128/4; 604/281; 148/402
[58] Field of Search ............... 128/4, 6; 604/281, 291; 148/402

[56] References Cited

U.S. PATENT DOCUMENTS

| 3,890,977 | 6/1975 | Wilson | 128/418 |
| 4,427,000 | 1/1984 | Ueda | 128/6 |
| 4,601,283 | 7/1986 | Chikama | 128/4 |
| 4,742,817 | 5/1988 | Kawashima | 128/4 |

Primary Examiner—William H. Grieb
Attorney, Agent, or Firm—Ladas & Parry

[57] ABSTRACT

An endoscope includes a bending member having a shape memory alloy. A pair of heating current supplying wires and a pair of resistance detecting wires are connected at one end to the ends of the shape memory alloy. The other end of the heating current supplying wire is connected to a current supply circuit, and the other end of the resistance detecting wire is connected to a resistance detector. The resistance detector is constituted by a bridge circuit having a branch opened and the shape memory alloy is connected in the opened branch via the resistance detecting wires. A controller controls the current supply circuit according to the detected resistance. The current supply is effected by supplying a current pulse, and the amount of heating current and the bending degree can be controlled by controlling the pulse width of the current pulse. Since no heating current is supplied to the resistance detecting wires, the resistance thereof is not changed even when the shape memory alloy is heated by passing a heating current therethrough. Therefore, it is possible to precisely detect variation in the resistance of only the shape memory alloy member and measure the bending degree of the bending member.

46 Claims, 25 Drawing Sheets

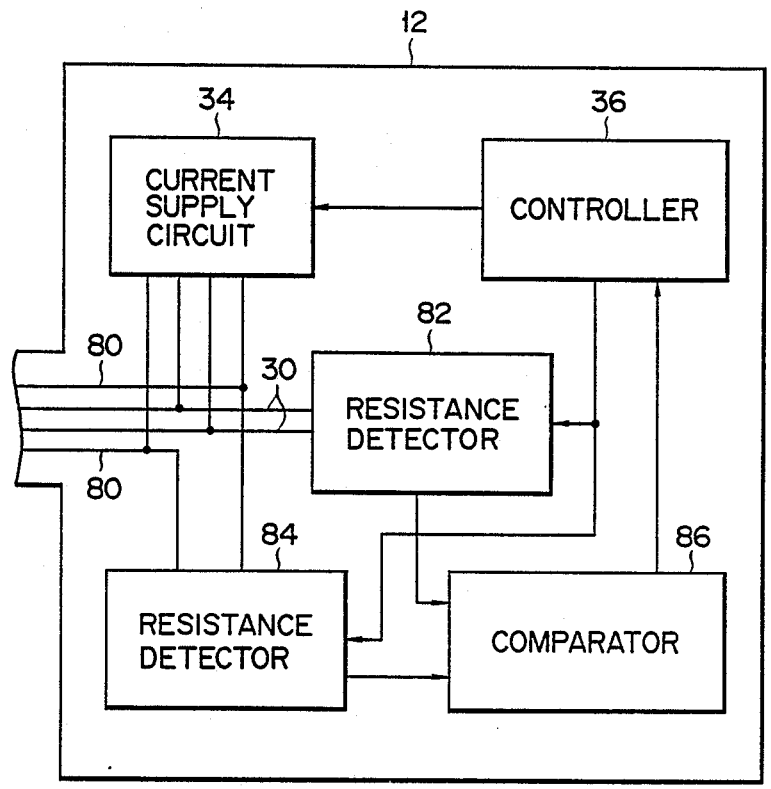
F I G. 10

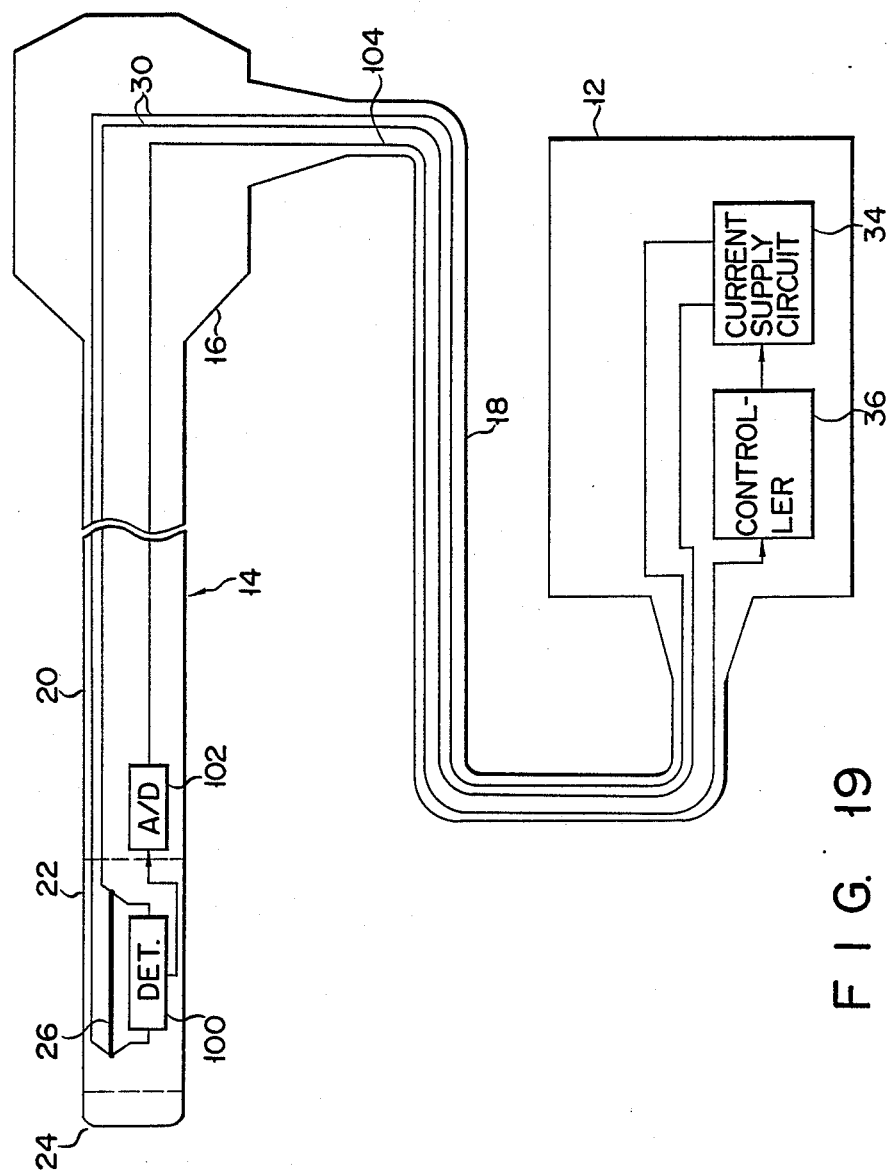
F I G. 19

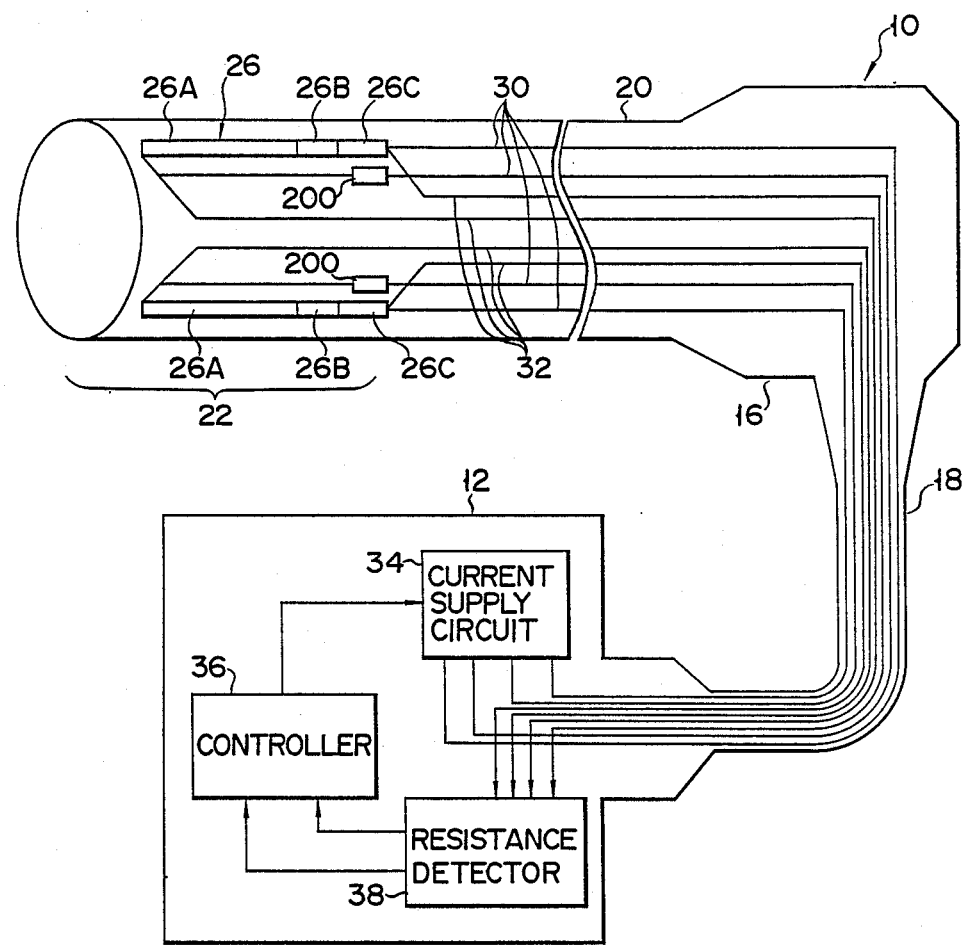
F I G. 25

R = R0 + r

R = R1 + r

R = r

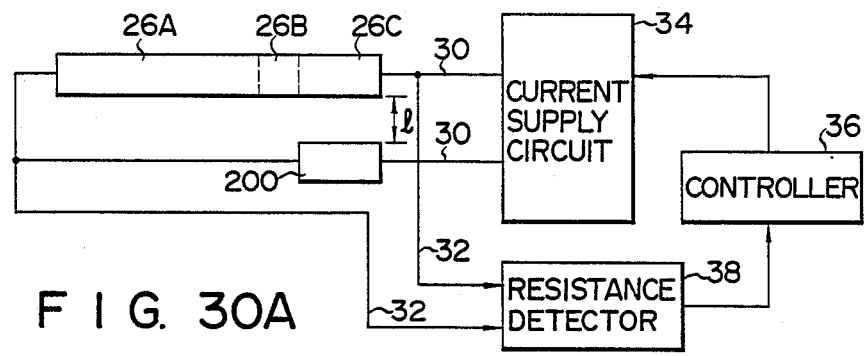
F I G. 30A
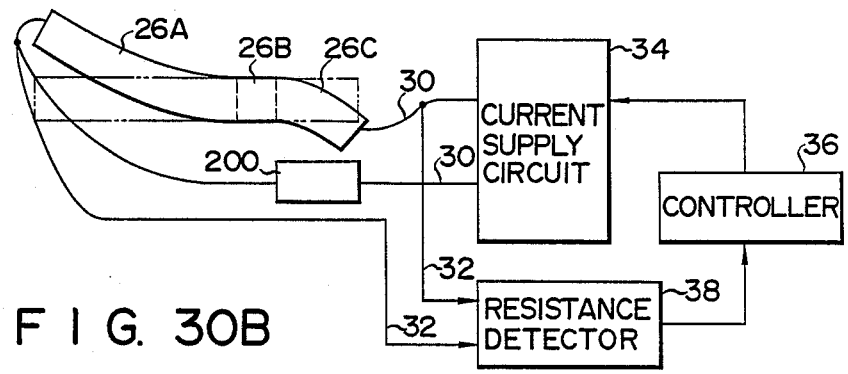
F I G. 30B
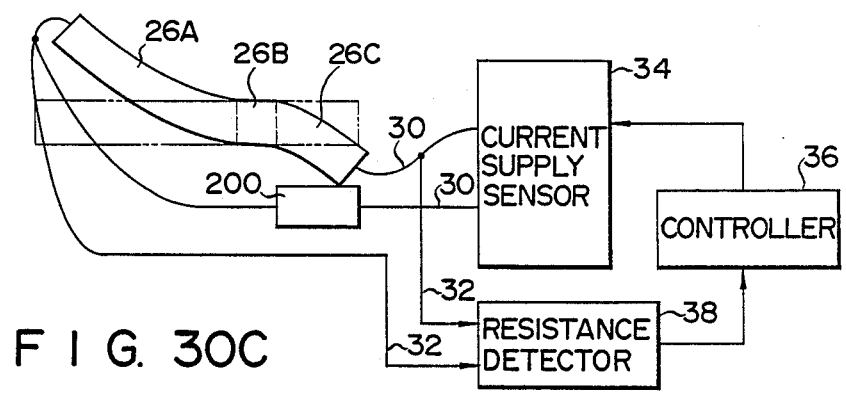
F I G. 30C

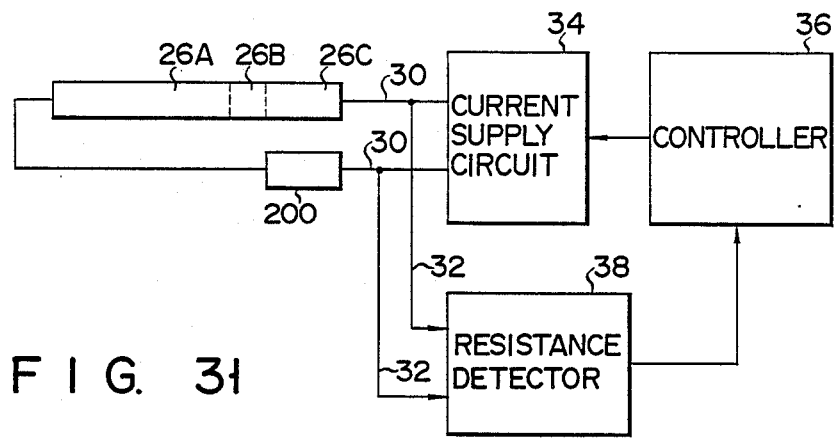
F I G. 31
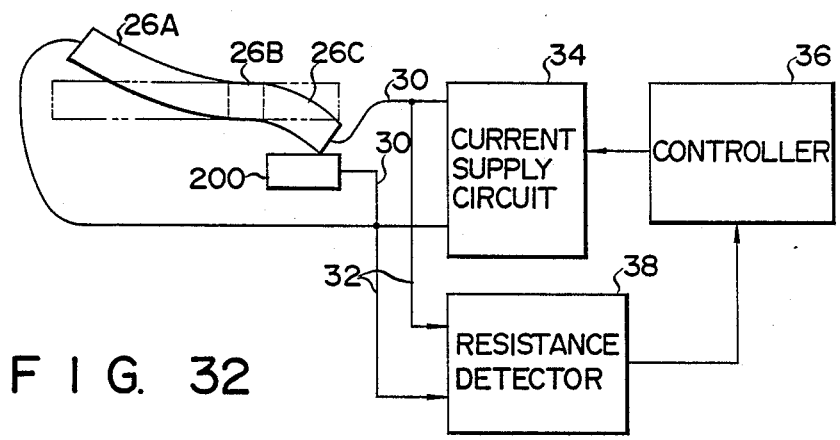
F I G. 32
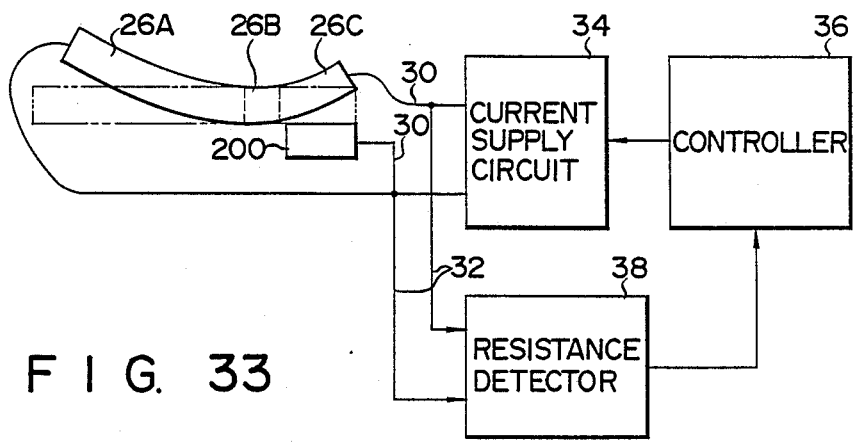
F I G. 33

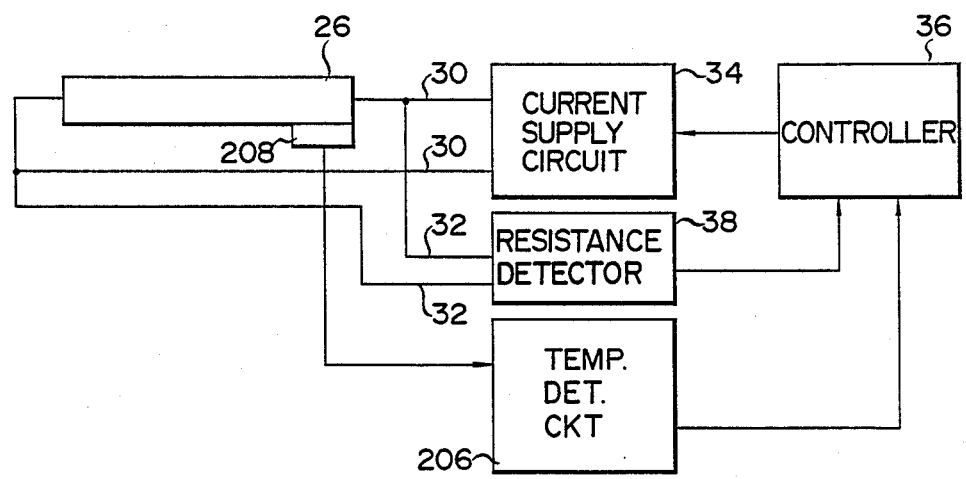
F I G. 36

ENDOSCOPE FOR AUTOMATICALLY ADJUSTING AN ANGLE WITH A SHAPE MEMORY ALLOY

BACKGROUND OF THE INVENTION

1. Field of the Invention

This invention relates to an actuator apparatus for driving a load or the like by utilizing the shape restoring function of shape memory alloy (SMA), and for example, to a memory shape actuator for use in a mechanism for bending the insertion end portion of an endoscope.

2. Description of the Related Art

In a general bending method used in the endoscope, a bending wire is inserted through the inserted portion with the tip end thereof fixed on the insertion end portion and the rear end connected to the knob of a manually operating section, and the knob is manually operated to pull or push the wire so as to bend the insertion end portion.

The above bending method has various problems that the construction is complex, the diameter of the insertion section is made large and a relatively large force is required to operate the knob. In order to solve these problems, a new method has been developed in which SMA is set inside the bending end portion of the endoscope and SMA is heated to show the shape restoring function by passing current therethrough. Such a method is disclosed in, for example, Japanese Patent Disclosure 59-48710 and Japanese patent application 61-276089 filed by the same applicant as that of this invention.

It is necessary to detect the bending degree of SMA in order to control the amount of current to be supplied to SMA. Since, in general, the resistance of SMA varies with the displacement thereof, the bending degree of SMA can be detected by detecting the resistance thereof.

In the prior art, a resistance detector is connected to a lead wire for heating SMA by passing current via SMA in order to detect the resistance of SMA, for example. Such a technology is disclosed in Japanese Patent Disclosure 62-26041. However, in the case where current is passed via SMA to heat the same, the lead wire is also heated and the resistance thereof is also changed. As a result, the detected resistance is influenced by variation in the resistance of the lead wire which is heated by passing current therethrough, and therefore it is impossible to precisely measure the resistance of SMA.

In many cases, the resistance detector is provided separately from the main body of the endoscope, e.g., in a light source unit, and the length of the insertion section and light guide cable of the endoscope may differ depending on the type of the endoscope. Therefore, the length of the lead wire differs depending on the type of the endoscope and the influence by the resistance of the lead wire on the measured resistance of SMA may vary depending not only on the temperature but also on the type of the endoscope. Further, SMA itself may have different resistances. Therefore, when a different endoscope is used, the detected resistance may vary, and it will be impossible to selectively connect a common light source unit to a plurality of endoscopes.

Further, since variation in the resistance of SMA due to the phase change of SMA is extremely small, it is difficult to precisely detect the resistance.

Therefore, it has been considered to amplify the resistance variation caused by the phase change. In general, in order to increase the resistance of SMA, the cross-sectional area thereof is reduced. However, in this case, the bending force by SMA will be weak. In a method disclosed in Japanese Patent Disclosure 60-175777, a plurality of coils of SMA are arranged in parallel in order to attain a sufficiently large bending force using SMA with a reduced cross-sectional area. However, in this case, it is necessary to provide a large space for the plurality of SMA coils, increasing the diameter of the insertion end portion.

SUMMARY OF THE INVENTION

An object of this invention is to precisely detect the resistance of shape memory alloy used in a shape memory actuator.

Another object of this invention is to provide an endoscope in which a bending section having shape memory alloy mounted on an insertion end portion is provided and the shape memory alloy is heated by passing current therethrough while detecting the resistance of the shape memory alloy so that the bending portion may be bent by a desired angle and automatically inserted into a body cavity.

Another object of this invention is to provide an endoscope system which comprises an endoscope body including a bending section having shape memory alloy mounted on an insertion end portion and a light source device arranged separately from the endoscope body and provided to bend the bending section by passing current through the shape memory alloy and detect the resistance of the shape memory alloy, and which can precisely detect the resistance of the shape memory alloy in accordance with the type of the endoscope relating to the length of the insertion section and the type of the shape memory alloy, making it possible to precisely control the bending degree of the end portion.

The shape memory actuator of this invention includes means for detecting the resistance of the shape memory alloy irrespective of the resistance of the lead wire.

The endoscope according to this invention includes means for detecting the resistance of the shape memory alloy in the bending section provided in the insertion end portion and control means for comparing the detected resistance with a desired value and causing energizing means to control a current passing via the shape memory alloy such that the detected resistance becomes equal to the desired value.

The endoscope system of this invention comprises an endoscope body including a bending section having shape memory alloy mounted on an insertion end portion and light source device detachably connected to the endoscope body to detect the resistance of the shape memory alloy by selectively using an optimum detection circuit for each type of the endoscope body.

BRIEF DESCRIPTION OF THE DRAWINGS

FIG. 10 is a block diagram of a modification of the fourth embodiment;

FIG. 19 is a block diagram of an endoscope device according to a seventh embodiment of this invention;

FIG. 25 is a block diagram of an endoscope device according to a tenth embodiment of this invention;

FIGS. 30A to 30C are diagrams showing displacements of SMA of a second modification of the tenth embodiment;

FIG. 31 is a block diagram of a third modification of the tenth embodiment;

FIG. 32 is a block diagram of a fourth modification of the tenth embodiment;

FIG. 33 is a block diagram of a fifth modification of the tenth embodiment;

FIG. 36 is a block diagram of an eighth modification of the tenth embodiment.

DETAILED DESCRIPTION OF THE PREFERRED EMBODIMENT

There will now be described embodiments of this invention with reference to the accompanying drawings.

Figure 1:
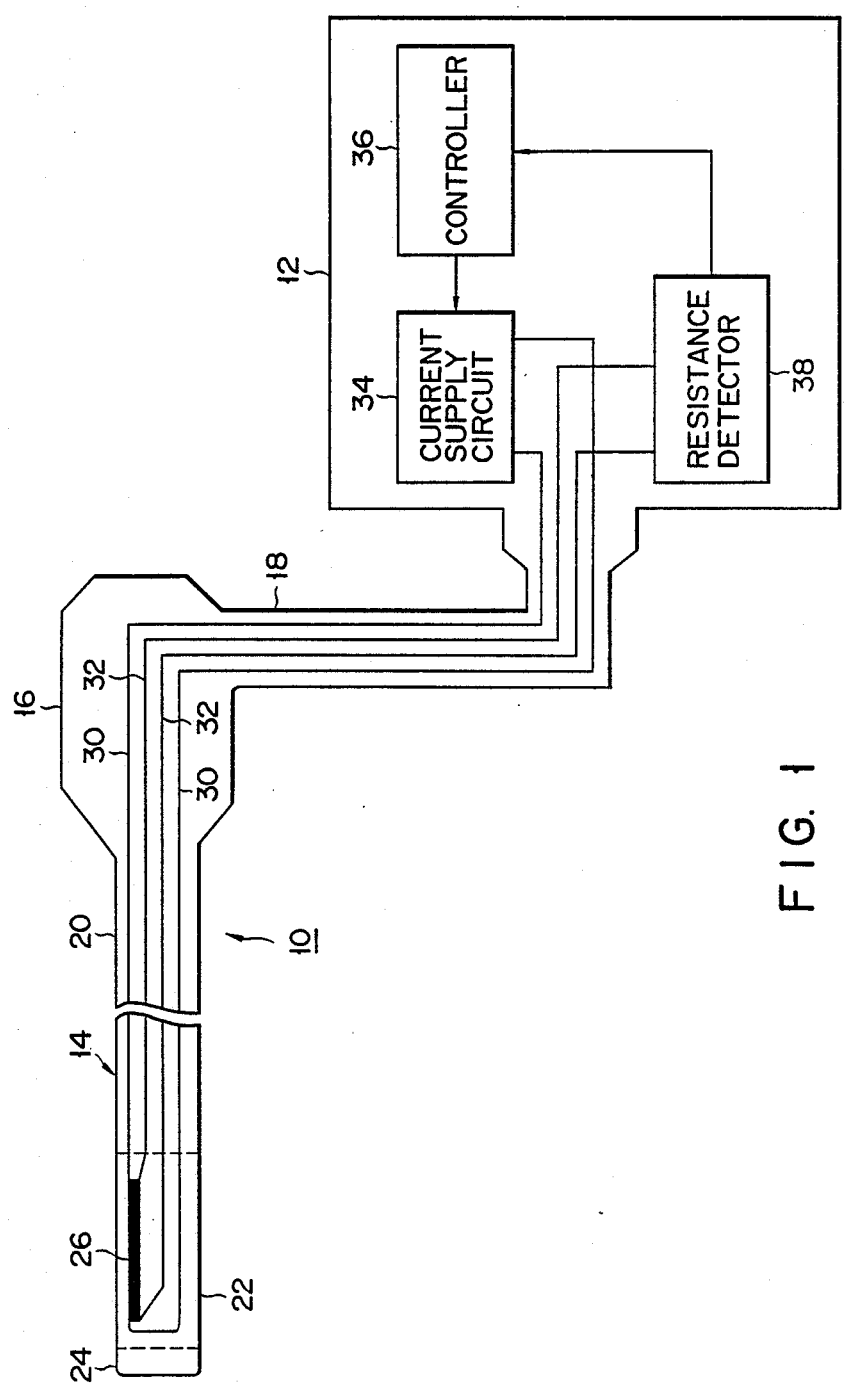
FIG. 1 is a block diagram of an endoscope device according to a first embodiment of this invention.

FIG. 1 is a block diagram of a first embodiment. The first embodiment includes endoscope 10 and light source device 12 which are detachably connected to each other. Light source device 12 can be commonly connected to a plurality of endoscopes of different types. In this case, endoscope 10 may be used for medical treatment to observe the body cavity, or for industrial application to observe the internal state of narrow tubes, internal narrow space in machines or the like.

Endoscope 10 is constituted by integrally connecting operating section 16, inserting section 14 and universal cord section 18. In this case, since an optical system such as an image guide fiber and a light guide fiber is not directly related to this invention, the explanation and the diagram thereof are omitted. Inserting section 14 includes flexible tube 20, bending member 22 provided at the tip end of tube 20 and tip end forming portion 24 forming the end surface of bending member 22. Bending member 22 has shape memory alloy (SMA) 26 provided therein. SMA 26 is formed of, for example, Ti-Ni alloy, Cu-Zn-Al alloy. SMA 26 is formed in a strip form, and arranged to extend in an axial direction of bending member 22. SMA 26 may be formed in a coil form. SMA 26 is processed to previously memorize a desired bent shape. Thus, SMA 26 is restored to the memorized shape at a transformation temperature or a temperature higher than 40° C. At a normal temperature, SMA 26 is kept in the straight strip form. Tip forming portion 24 is formed of metal.

Universal cord section 18 is connected to light source device 12 and includes a light guide fiber, a pair of heating current supplying wires 30 and a pair of resistance detecting wires 32. Heating current supplying wires 30 are connected at one end to the respective ends of SMA 26 and resistance detecting wires 32 are also connected at one end to the respective ends of SMA 26.

Light source device 12 has a function attained by current supply circuit 34, controller 36 and resistance detector 38 in addition to a unit performing an ordinary light source function (not shown). The other ends of heating current supplying wires 30 are connected to current supply circuit 34, and the other ends of resistance detecting wires 32 are connected to resistance detector 38. Resistance detector 38 is formed of a bridge circuit having SMA 26 connected as one of four branches. Current supply circuit 34 supplies an energizing current pulse to SMA 26 via heating current supplying wires 30, and controller 36 controls the supply of current pulse from current supply circuit 34 such that the detected resistance becomes equal to a resistance corresponding to the desired bending degree.

Thus, current supply circuit 34 supplies an energizing current to SMA 26 via current supplying wires 30 to heat SMA 26 above the transformation temperature and restore or bend SMA 26 to the memorized shape, thereby to bend bending member 22.

In this case, the resistance of SMA 26 is detected at the off-time of the current pulse by means of resistance detector 38 by making use of wires 32 which are connected to SMA 26 and arranged separately from current supplying wires 30. Since wires 32 are not energized, the resistance of wires 32 is not changed even when SMA 26 is heated by passing current therethrough. Thus, the resistance of SMA 26 is detected by using the wires different from the heating current supplying wires, and therefore variation in the resistance of SMA 26 can always be precisely detected. Since it is known in the art that the resistance of SMA is changed in accordance with the phase-change from the martensite or rhombohedral phase at the low temperature side to the austenite phase at the high temperature side, it is possible to determine the bending degree of bending member 22 based on the detected resistance.

As described above, according to the first embodiment, since the resistance of wires 32 is not changed, only variation in the resistance of SMA 26 can be detected, permitting the bending degree of bending member 22 to be precisely detected so that the bending degree can be precisely controlled.

Now, other embodiments are explained. In the following embodiments, portions corresponding to those in FIG. 1 are denoted by the same reference numerals and the detail explanation thereof are omitted.

Figure 2:
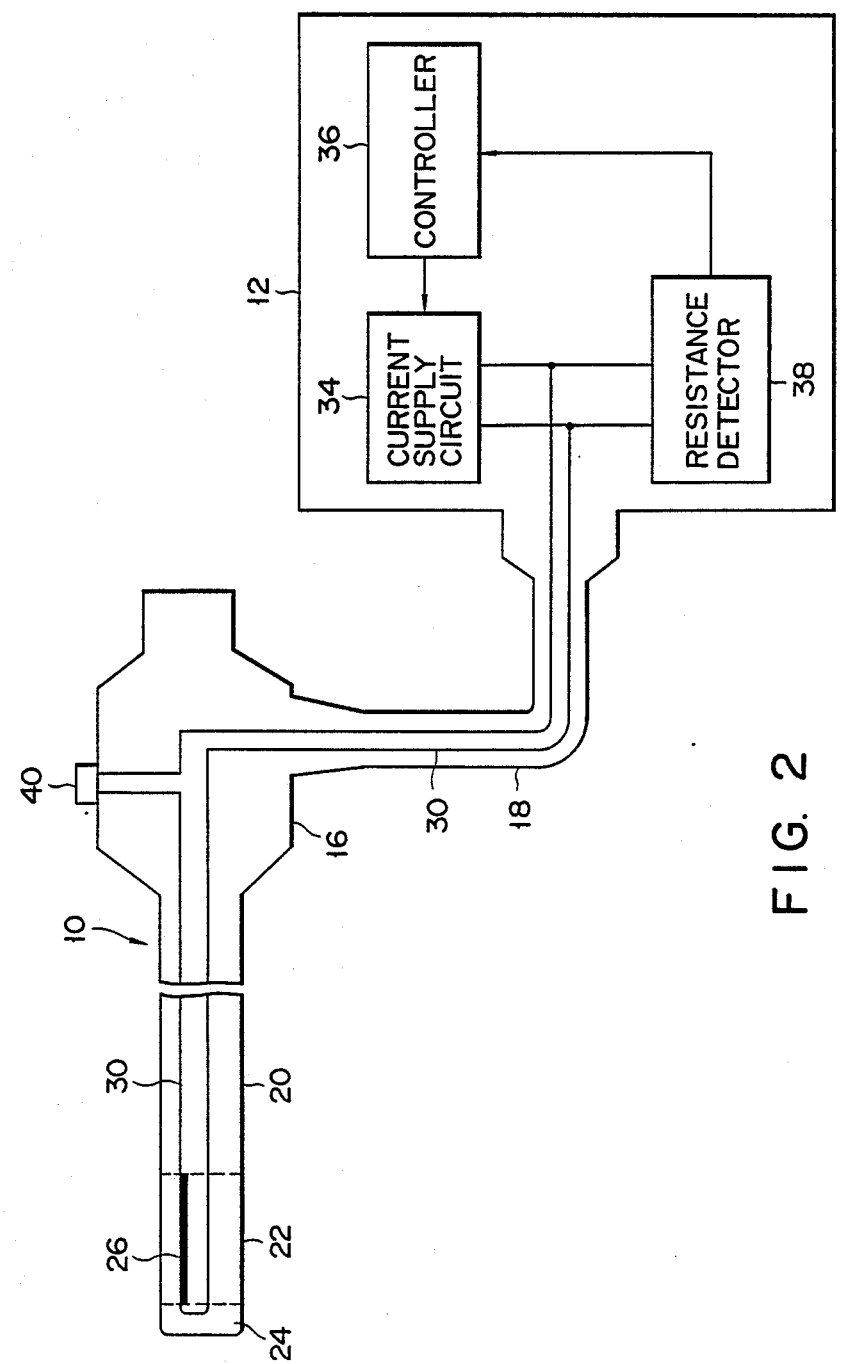
FIG. 2 is a block diagram of an endoscope device according to a second embodiment of this invention.

FIG. 2 is a block diagram of a second embodiment. The second embodiment is different from the first embodiment in that resistance detecting wires 32 are not provided in endoscope 10 and only heating current supplying wires 30 are provided. Switch 40 for making or breaking the current path of heating current supplying wires 30 is arranged in operating section 16. Wires 30 are connected to both current supply circuit 34 and resistance detector 38 in light source device 12.

Figure 3:
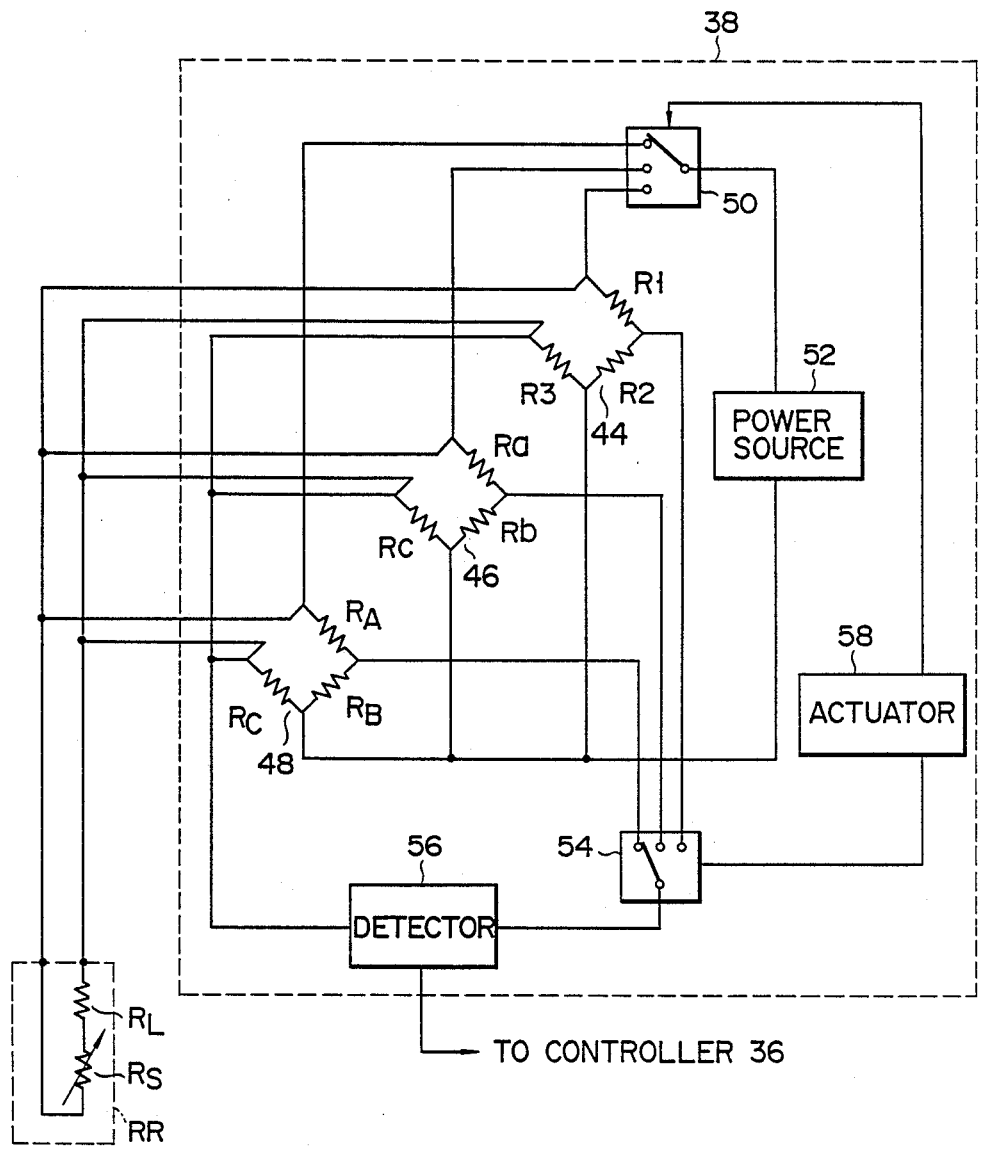
FIG. 3 is a block diagram of a resistance sensor in the second embodiment.

The feature of the second embodiment lies in resistance detector 38, and the circuit of resistance detector 38 is shown in FIG. 3. Resistance detector 38 includes three bridge circuits 44, 46 and 48 having different resistances. Resistors R1 to R3; Ra to Rc; or RA to RC are connected on three branches of each of the bridge circuits, and no resistor is connected on the remaining branch or the remaining branch is opened. That is, combined resistor RR of resistor Rs of SMA 26 in endoscope 10 and resistor RL of wires 30 is commonly connected in the remaining branch of each bridge circuit only when endoscope 10 is connected to light source device 12.

Connection nodes between resistor RR and resistors R1, Ra and RA are connected to three fixed contacts of selector 50 which has a movable contact connected to power source 52. The other ends of resistors R1, Ra and RA (connection nodes between resistors R1, Ra and RA and corresponding resistors R2, Rb and RB) are connected to three fixed contacts of selector 54 which has a movable contact connected to detector 56.

Connection nodes between resistor RR and resistors R3, Rc and RC are connected to detector 56, and connection nodes between resistors R3, Rc and RC and corresponding resistors R2, Rb and RB are connected to power source 52.

Selectors 50 and 54 are synchronously controlled by means of actuator 58. That is, detector 56 is connected only one of bridge circuits 44, 46 and 48 via selector 54 and only the selected bridge circuit is connected to power source 52 via selector 50. This operation is effected because the resistance of resistor RR in a different endoscope is different. In general, resistance RL varies depending on the length and the material of wires 30 and resistance Rs varies by variation in the resistance of SMA 26 itself. Therefore, it is necessary to select a bridge circuit suitable for the type of endoscope in order to suppress a measurement error to a minimum.

Thus, in the second embodiment, selectors 50 and 54 are synchronously controlled by means of actuator 58 according to the type of the endoscope connected to light source device 12, so that each of the movable contacts of selectors 50 and 54 can be selectively connected to one of bridge circuits 44, 46 and 48.

In operation, switch 40 is turned on to permit a current pulse to be supplied from current supply circuit 34 to SMA 26 via wires 30. The resistance of SMA 26 is detected when the current pulse is at an off level. The resistance of SMA 26 is detected according to the degree of unbalance in the bridge circuit caused by variation in the resistance of SMA 26 when it is heated. Current supplying operation is effected so as to set the detected resistance equal to a previously set resistance and keep it unchanged.

According to this embodiment, even if the resistances of the SMA and wires for each endoscope to be used are changed, the bending degree can be precisely detected by selectively using a bridge circuit suitable for the endoscope.

Figure 4:
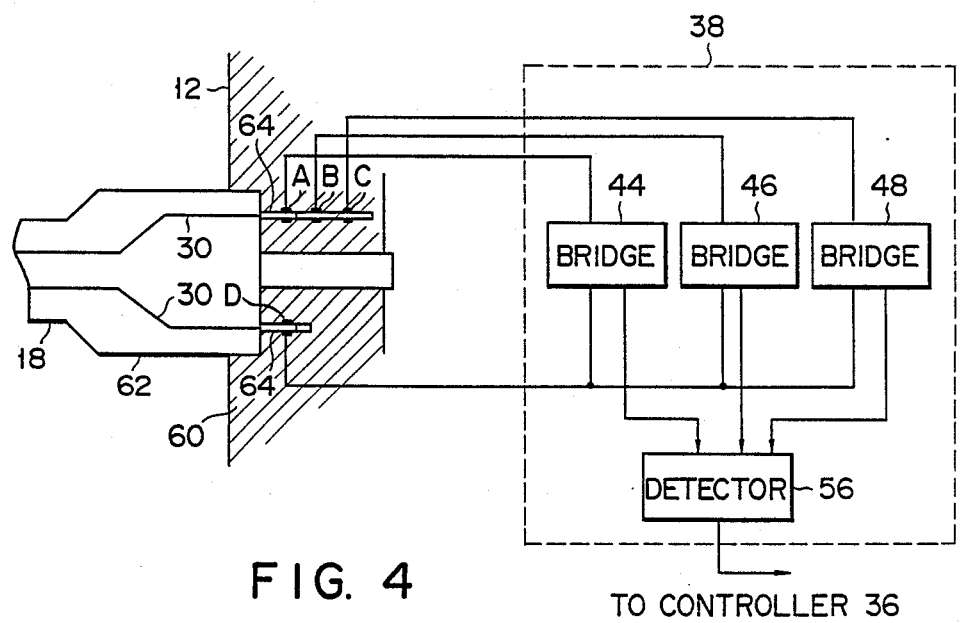
FIG. 4 is a block diagram of a first modification of the second embodiment.

FIG. 4 is a first modification of resistance detector 38 in the second embodiment. Contacts A, B and C for bridge circuits 44, 46 and 48 are provided at different depths in a hole of socket 60 of light source device 12. That is, each of contacts A, B and C is connected to one end of a corresponding one of bridge circuits 44, 46 and 48 (one end of resistors R1, Ra and RA in FIG. 3). The other ends of bridge circuits 44, 46 and 48 (one end of resistors R3, Rc and RC in FIG. 3) are commonly connected to contact D provided in another hole of socket 60. Further, connector 62 of endoscope 10 has projected pins 64 with lengths determined by the type of the endoscope used.

In the above modification, pin 64 is connected to one of contacts A, B and C provided in socket 60 when endoscope 10 is connected to light source device 12. Thus, only one of bridge circuits 44, 46 and 48 is selected.

Figure 5:
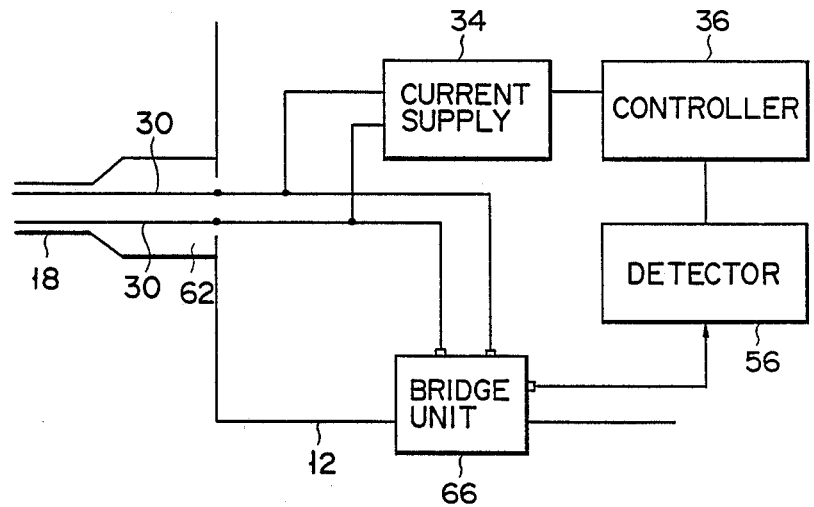
FIG. 5 is a block diagram of a second modification of the second embodiment.

FIG. 5 is a second modification of resistance detector 38 in the second embodiment. In this modification, instead of using a plurality of bridge circuits, bridge circuit units 66 each of which includes a corresponding one of the above-described bridge circuits and the power source and can be detachably connected to endoscope 10 is used. When the endoscope is connected to the light source device, bridge circuit unit 66 suitable for the endoscope used is selected and connected to light source device 12. In this case, the same effect as in the second embodiment can be obtained.

A third modification of the second embodiment is formed by combining endoscope 10 of the first embodiment and resistance detector 38 of the second embodiment. That is, SMA 26 is connected to resistance detector 38 through resistance detecting wires 32.

Figure 6:
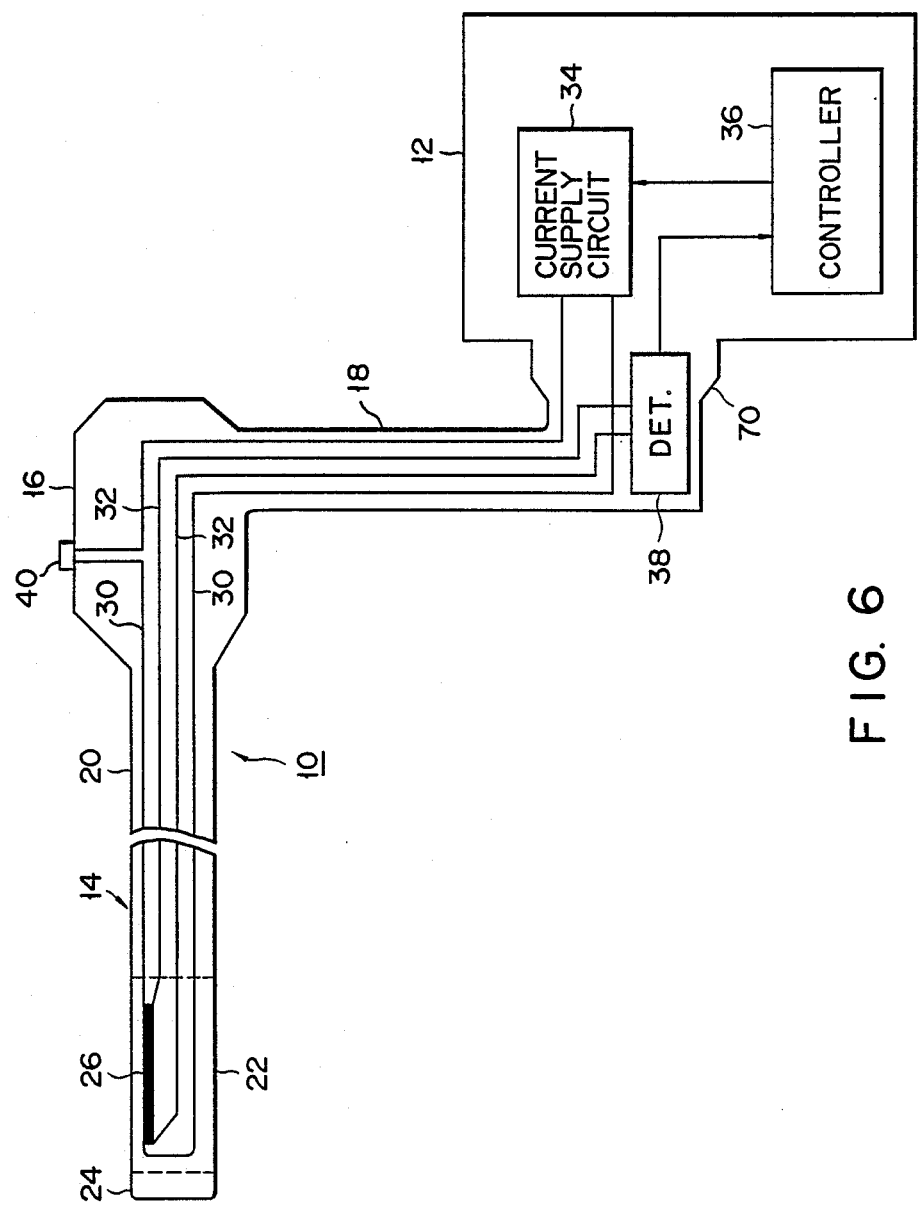
FIG. 6 is a block diagram of an endoscope device according to a third embodiment of this invention.

FIG. 6 is a block diagram of a third embodiment. The third embodiment is formed of the same constituents as in the first embodiment, but in the third embodiment, resistance detector 38 is not provided in light source device 12 but in connector 70 of endoscope 10 for connecting endoscope 10 to light source device 12.

Figure 7:
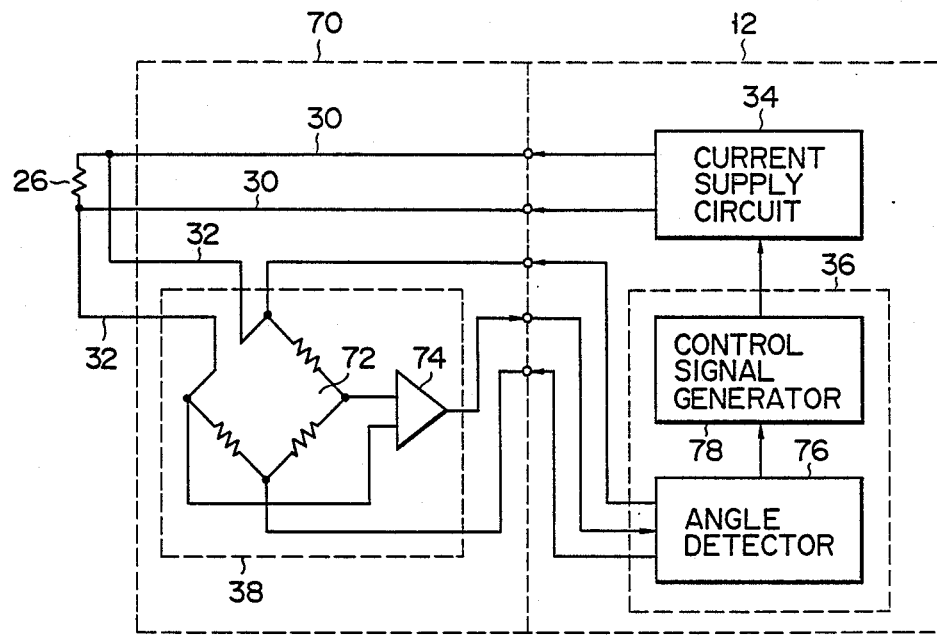
FIG. 7 is a block diagram of a resistance sensor in the third embodiment.

FIG. 7 is a circuit diagram of the FIG. 6 device. Resistance detector 38 includes bridge circuit 72 having SMA 26 connected as one branch via wires 32, and amplifier 74. The resistances of resistors constituting bridge circuit 72 are determined according to the resistance of SMA 26 of the endoscope. Controller 36 is constituted by angle detector 76 and control signal generator 78. An output of bridge circuit 72 is supplied to angle detector 76 via amplifier 74. Angle detector 76 supplies a bias voltage across bridge circuit 72, and further supplies an output signal to current supply circuit 34 via control signal generator 78.

In this embodiment, since resistance detector 38 suitable for the endoscope used is provided in connector 70 of the endoscope, the measurement can be effected without causing fluctuation for different endoscopes as in the second embodiment. Further, it is not necessary to selectively activate detector 38 and therefore the operability of the device is enhanced.

Figure 8:
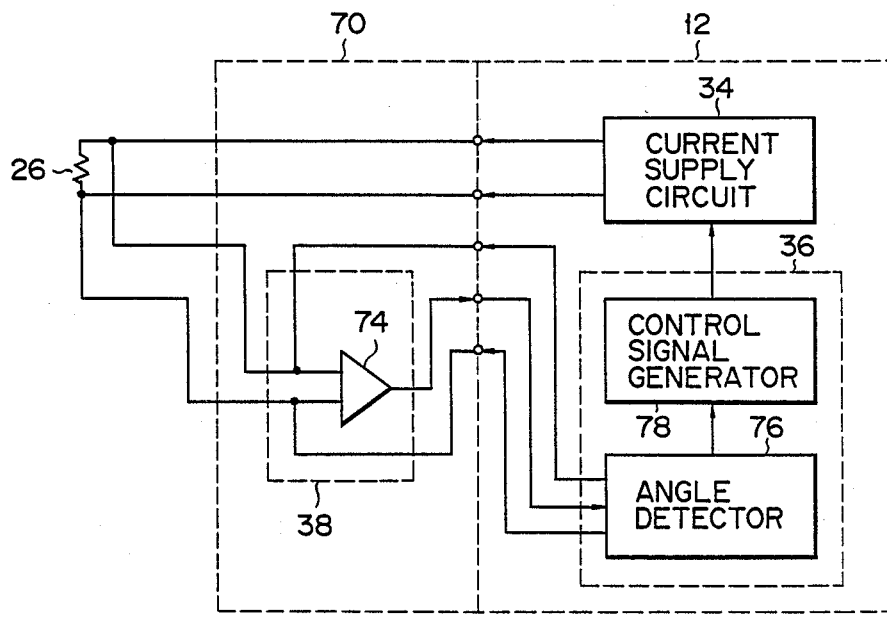
FIG. 8 is a block diagram of a resistance sensor in a modification of the third embodiment.

Resistance detector 38 is not limited to the bridge circuit, but can be constituted by amplifier 74 as shown in FIG. 8.

Figure 9:
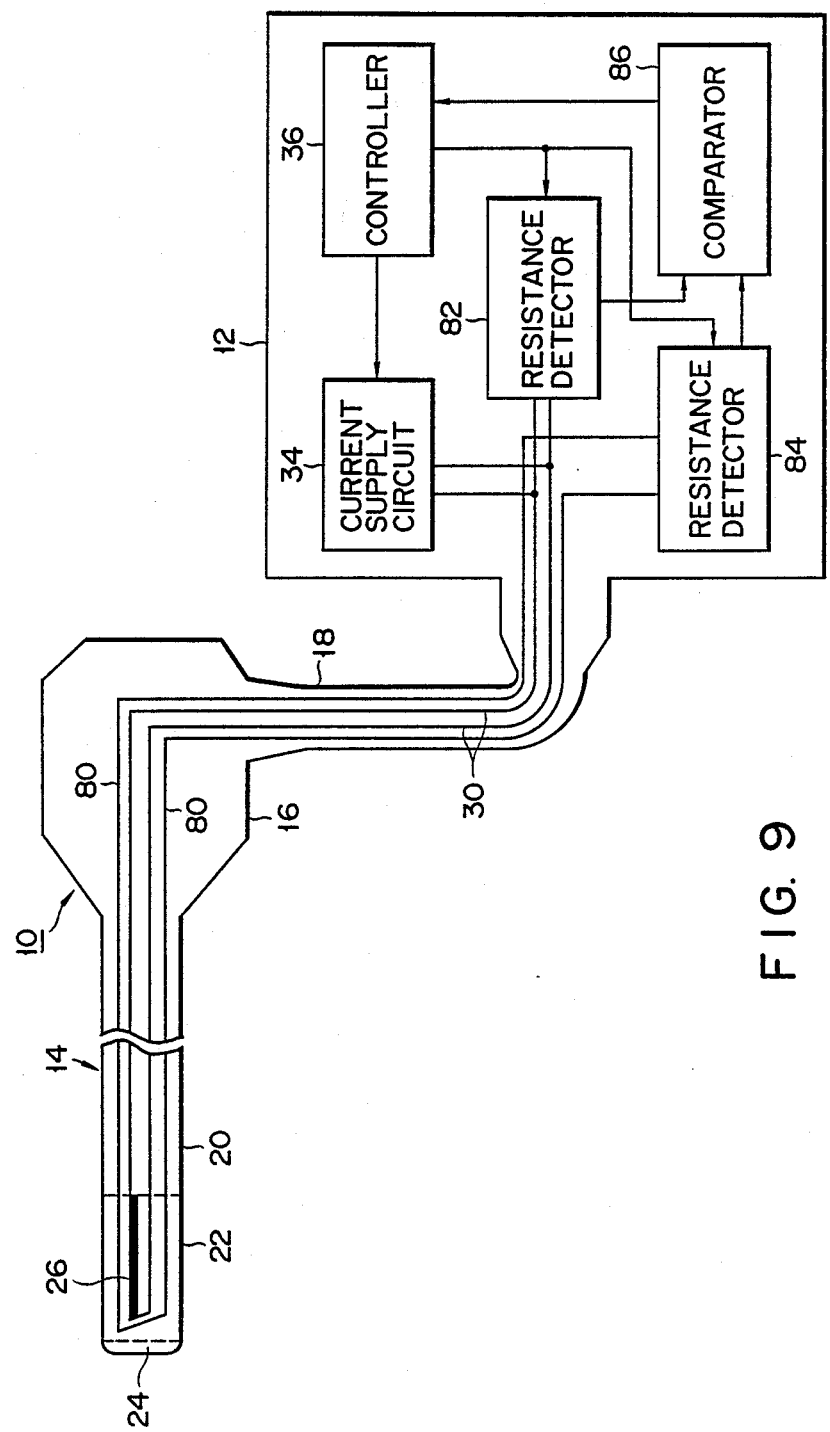
FIG. 9 is a block diagram of an endoscope device according to a fourth embodiment of this invention.

FIG. 9 is a block diagram of a fourth embodiment. Lead wire 80 for resistance detection is provided in endoscope 10 in addition to a pair of heating current supplying wires 30. Wire 80 is formed of the same material as wire 30, and is turned back near the tip end of inserting portion 14. Further, wire 80 is arranged in close relation to wires 30 so that wires 30 and 80 may have substantially the same factors such as the total length and the temperature which will influence the resistance thereof.

Light source device 12 includes first and second detectors 82 and 84. First resistance detector 82 and current supply circuit 34 are connected to wire 30. Second resistance detector 84 is connected to wire 80. Outputs of resistance detectors 82 and 84 are supplied to comparator 86 which in turn detects and supplies the difference between the input signals.

In this embodiment, detector 82 detects the sum of the resistances of SMA 26 and wire 30, and detector 84 detects the resistance of wire 80. Since the resistance of wire 30 is substantially the same as that of wire 80, the resistance of SMA 26 can be detected by detecting the difference between the sum of the resistances of wire 30 and SMA 26 and the resistance of wire 80 by means of comparator 86. Thus, the resistance of SMA 26 can be precisely detected without receiving any influence of variation in the resistance of wire 30 caused by passing current therethrough. Further, detectors 82 and 84 are constructed to detect the resistance in response to a signal from controller 36 at the off time of the current pulse.

FIG. 10 is a circuit diagram of a modification of the fourth embodiment. In this modification, wire 80 as well as wire 30 is connected to current supply circuit 34. With this construction, wires 30 and 80 are heated at substantially the same rate when current is passed therethrough, thereby making it possible to precisely detect the resistance of SMA 26. Further, if wires 30 and 80 are twisted together, the resistances thereof can be set closer to each other.

Figure 11:
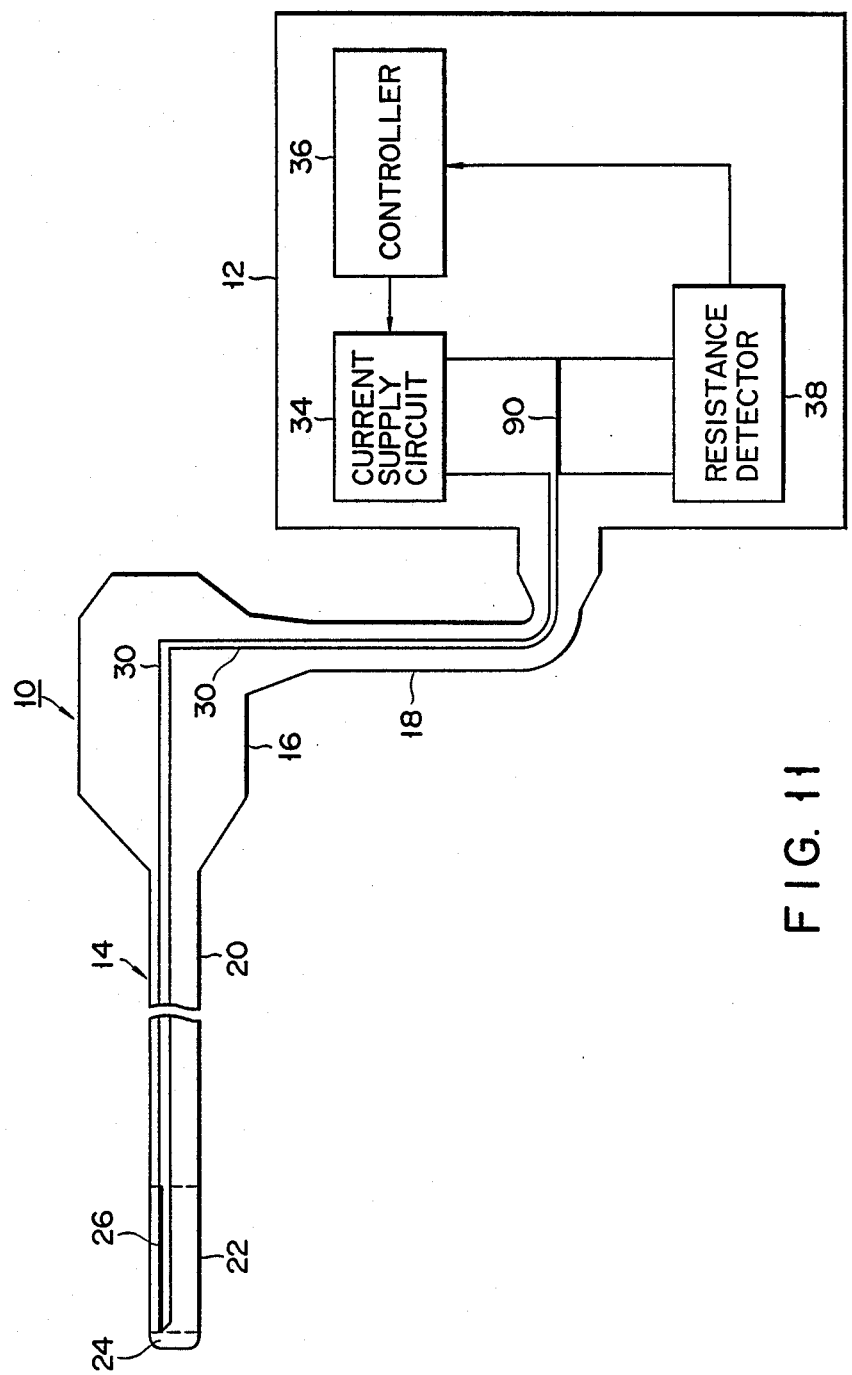
FIG. 11 is a block diagram of an endoscope device according to a fifth embodiment of this invention.

FIG. 11 is a block diagram of a fifth embodiment. Light source device 12 includes second SMA 90 in addition to current supply circuit 34, controller 36 and resistance detector 38. Second SMA 90 is formed of the same material as first SMA 26 and is processed to have the same shape memory function or the same characteristics as first SMA 26. Second SMA 90 is series-connected with wire 30, and both ends of second SMA 90 are connected to resistance detector 38.

Figure 12:
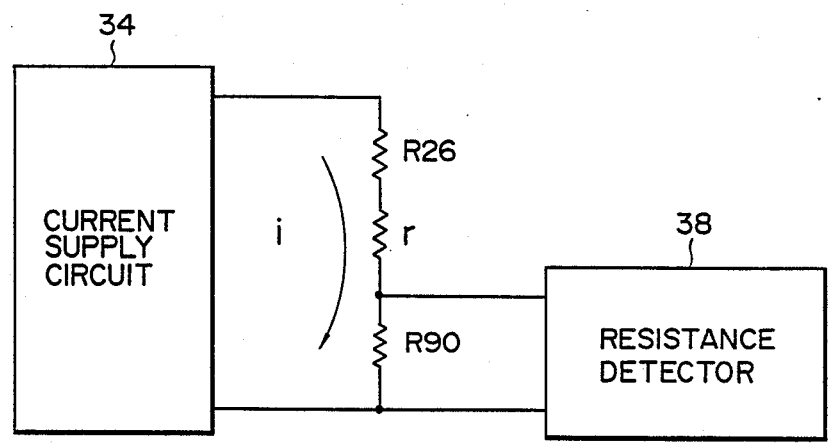
FIG. 12 is an equivalent circuit diagram of the fifth embodiment.

FIG. 12 is an equivalent circuit of the FIG. 11 device, R26, R90 and r respectively denote the resistances of SMA 26, SMA 90 and wire 30. As is clearly seen from FIG. 12, SMA 26 is series-connected with SMA 90 via wire 30, and resistance detector 38 is connected in parallel with SMA 90. Therefore, the same amount of current i flows via SMA 26 and SMA 90, and resistance detector 38 does not detect the resistance of wire 30 but detects the resistance of only SMA 90.

With this construction, when current is supplied to SMA 26 in order to bend bending member 22, SMA 90 of light source device 12 is also heated by the current supply and can be bent in the same manner as SMA 26. Variation in the resistance of SMA 90 due to the deformation is detected by means of detector 38. That is, since the resistance of SMA 90 having the same characteristics as SMA 26 arranged inside bending member 22 is detected without using wires 30, variation in the resistance of only SMA 26 can be precisely detected without receiving the influence of wires 30.

Figure 13:
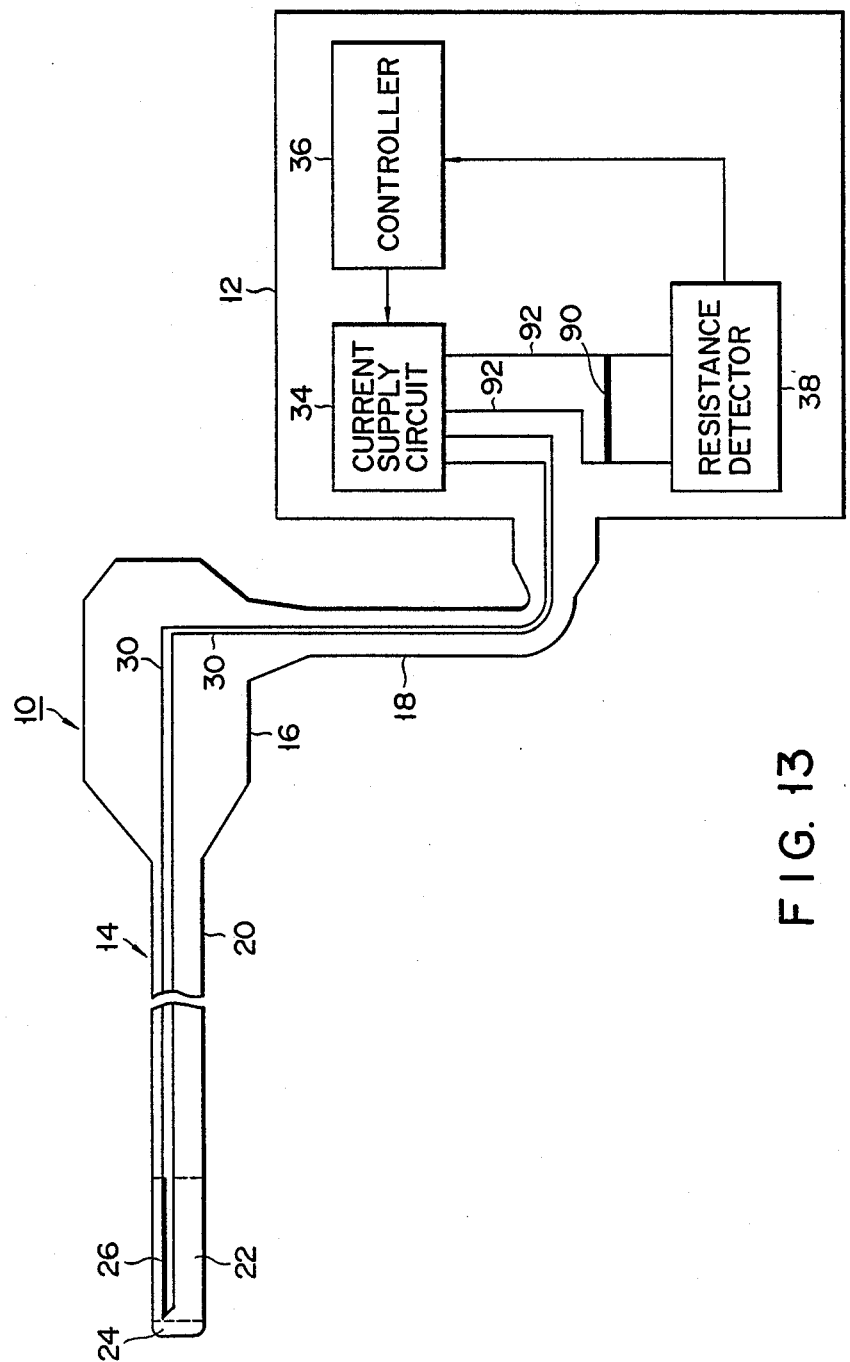
FIG. 13 is a block diagram of a modification of the fifth embodiment.

FIG. 13 is a block diagram of a modification of the fifth embodiment.

In this embodiment, SMA 26 is connected to current supply circuit 34 via wire 30, and SMA 90 is connected to current supply circuit 34 and resistance sensor 38 via a pair of wires 92 which are provided separately from wires 30.

Figure 14:
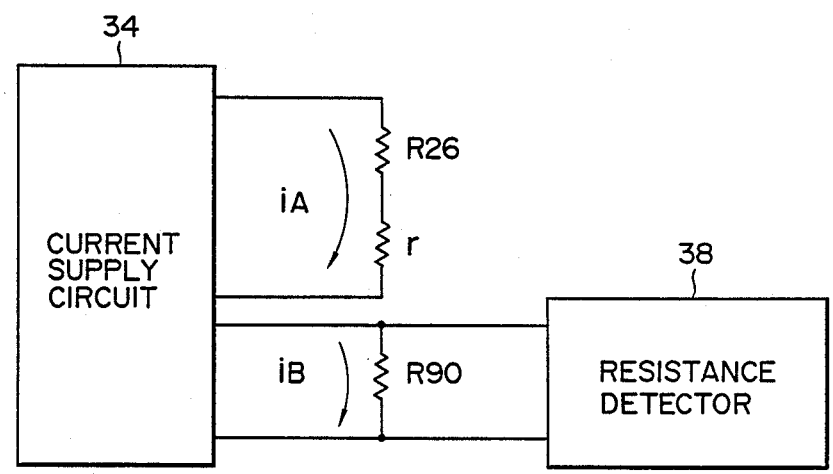
FIG. 14 is an equivalent circuit diagram of a modification of the fifth embodiment.

FIG. 14 is an equivalent circuit of the FIG. 13 embodiment.

With this construction, if current iA which is supplied from current supply circuit 34 to SMA 26 and wires 30 is set equal to current iB which is supplied to SMA 90, the same effect as described above can be obtained.

Figure 15:
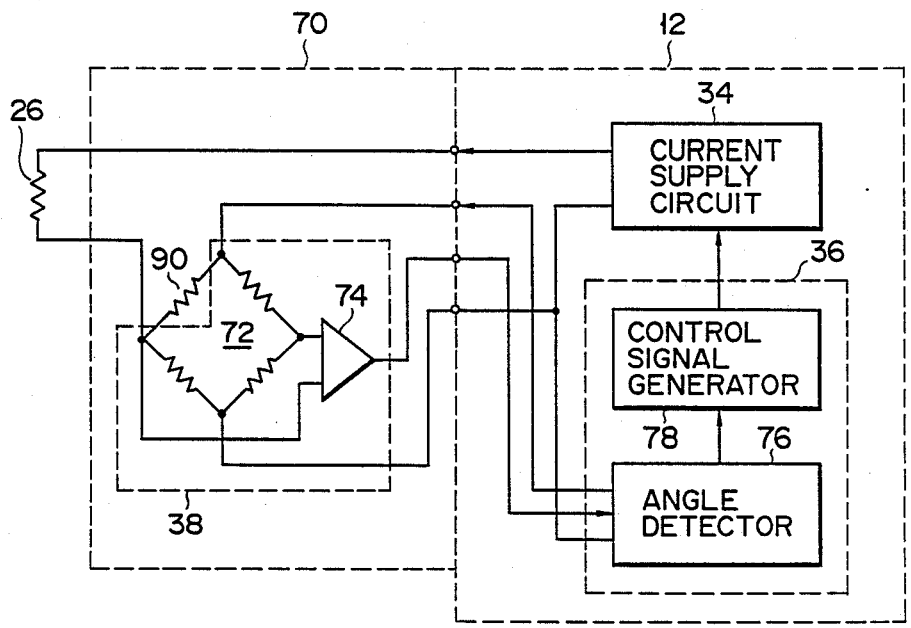
FIG. 15 is a block diagram of an endoscope device according to a sixth embodiment of this invention.

FIG. 15 is a block diagram of a sixth embodiment. In the sixth embodiment, second SMA 90 of the fifth embodiment shown in FIG. 11 and resistance detector 38 are arranged in connector 70 of endoscope 10 for connecting endoscope 10 to light source device 12. In the FIG. 15 embodiment, resistance detector 38 is constituted by bridge circuit 72 and amplifier 74 in the same manner as in the third embodiment.

In this embodiment, since resistance detector 38 is provided in each endoscope, the resistance of SMA 26 can be precisely detected even if the resistance of SMA 26 varies for respective endoscope.

Figure 16:
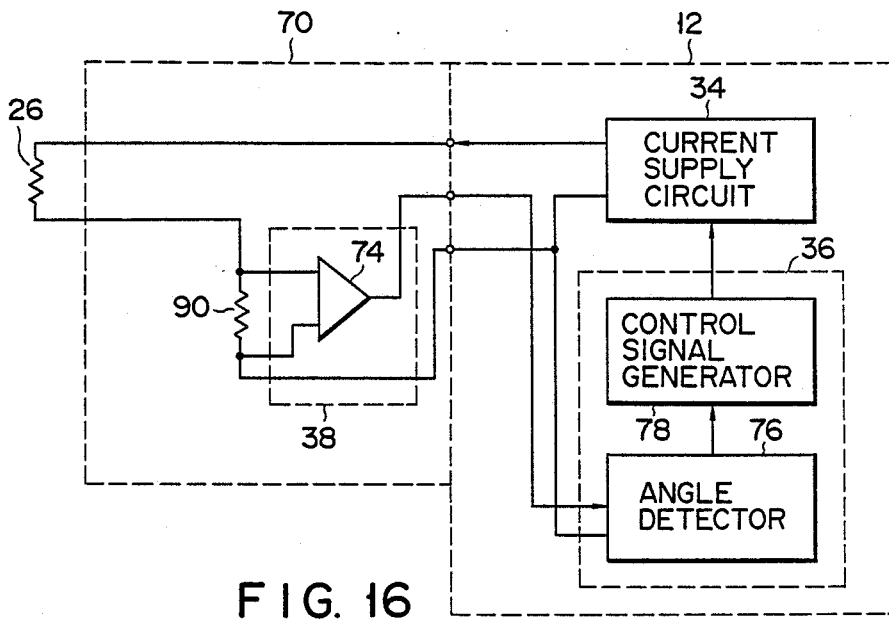
FIG. 16 is a block diagram of a modification of the sixth embodiment.

FIG. 16 is a block diagram of a modification of the sixth embodiment. In this embodiment, resistance detector 38 is constituted only by amplifier 74.

Figure 17:
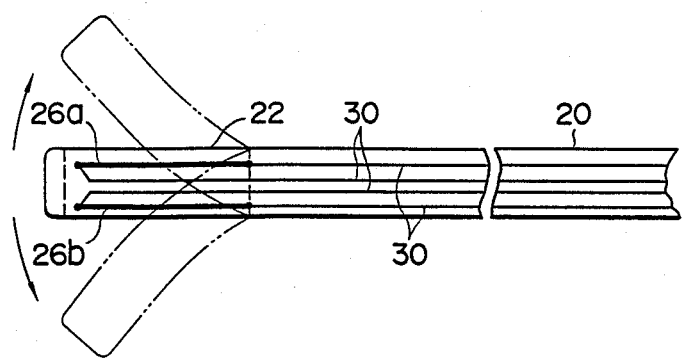
FIG. 17 is a block diagram of a modification of the first to sixth embodiments.

In the first to sixth embodiments, a single SMA is provided and the bending direction is limited to one direction, but a plurality of SMAs can be provided. FIG. 17 is a modification of the first to sixth embodiments in which two SMAs 26a and 26b are provided in parallel in bending member 22 and bending member 22 can be bent in upper and lower directions as shown by two-dot-dash lines.

Figure 18:
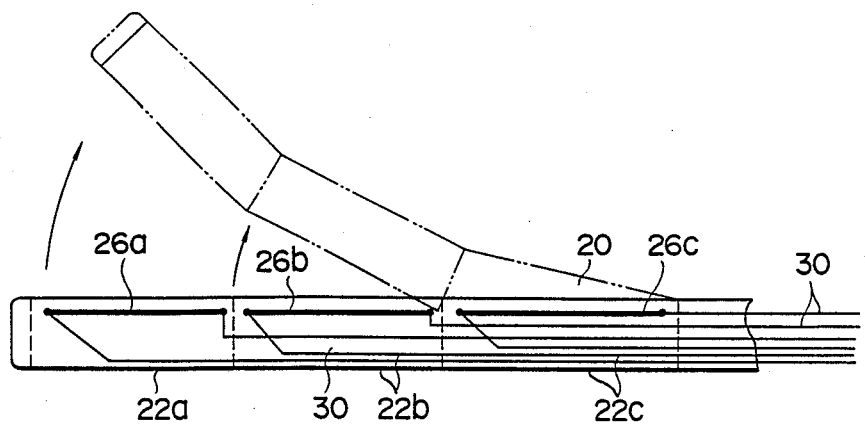
FIG. 18 is a block diagram of another modification of the first to sixth embodiments.

Further, in the first to sixth embodiments, bending member 22 is provided in a singular form, but two or more bending members 22 can be provided. FIG. 18 is a modification of the first to sixth embodiments in which three bending members 22a, 22b and 22c are serially connected. In this case, the maximum bending angle can be set large.

FIG. 19 is a block diagram of a seventh embodiment. In this embodiment, resistance detector 100 is provided in bending member 22 in addition to SMA 26. Resistance detector 100 is connected between both ends of SMA 26. An output of resistance detector 100 is supplied to controller 36 provided in light source device 12 via A/D converter 102 provided in inserting section 14 and wire 104 provided separately from heating current supplying wires 30. In the other respects, this embodiment is similar in construction to the first embodiment.

In this embodiment, resistance detector 100 is connected in parallel with SMA 26 to permit the resistance of only SMA 26 to be precisely detected. The detected resistance is converted to a corresponding digital value by means of A/D converter 102 arranged near detector 100, and then supplied to controller 36 via wire 104. Thus, the detected resistance can be correctly transmitted to controller 36 without receiving any influence by spurious noise and influence by variation in the length of universal cord section 18 and the inserting section of the endoscope.

Figure 20:
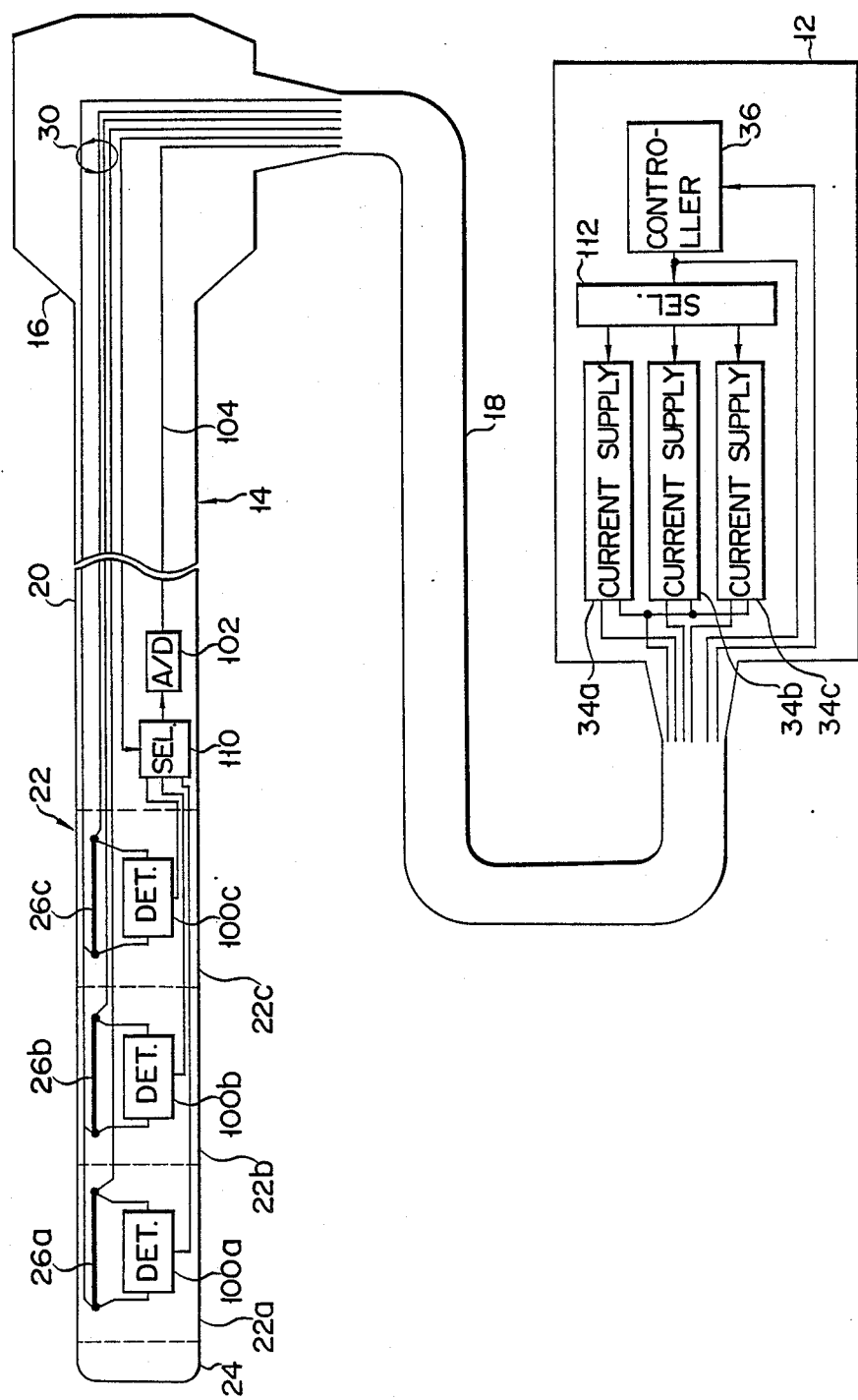
FIG. 20 is a block diagram of a modification of the seventh embodiment.

FIG. 20 is a modification of the seventh embodiment. In this modification, three bending members 22a, 22b and 22c are series-connected. SMAs 26a, 26b and 26c are respectively provided inside bending members 22a, 22b and 22c. Resistance detectors 100a, 100b and 100c are respectively connected in parallel with SMAs 26a, 26b and 26c. Detection signals from resistance detectors 100a, 100b and 100c are supplied to selector 110 which in turn selects and produces one of the received detection signals in response to a selection signal from controller 36. An output from selector 110 is supplied to controller 36 via A/D converter 102 and wire 104.

Three current supply circuits 34a, 34b and 34c corresponding to bending members 22a, 22b and 22c are arranged in light source device 12, and outputs from current supply circuits 34a, 34b and 34c are supplied to SMAs 26a, 26b and 26c via wires 30. Current supply circuits 34a, 34b and 34c are connected to selector 112 which selects one of current supply circuits 34a, 34b and 34c. An energization signal is supplied via the selected current supply circuit. Selector 112 is also controlled by an output signal of controller 36, and selectors 110 and 112 are synchronously operated.

This modification is advantageous in that single A/D converter 102 and single wire 104 for detection signal transmission can be used without causing any problem even when a plurality of bending members are provided.

Further, in the seventh embodiment, it is possible to arrange a plurality of SMAs in parallel in the bending member as shown in FIG. 17 so as to bend the bending member in various directions.

Figures 21, 22:
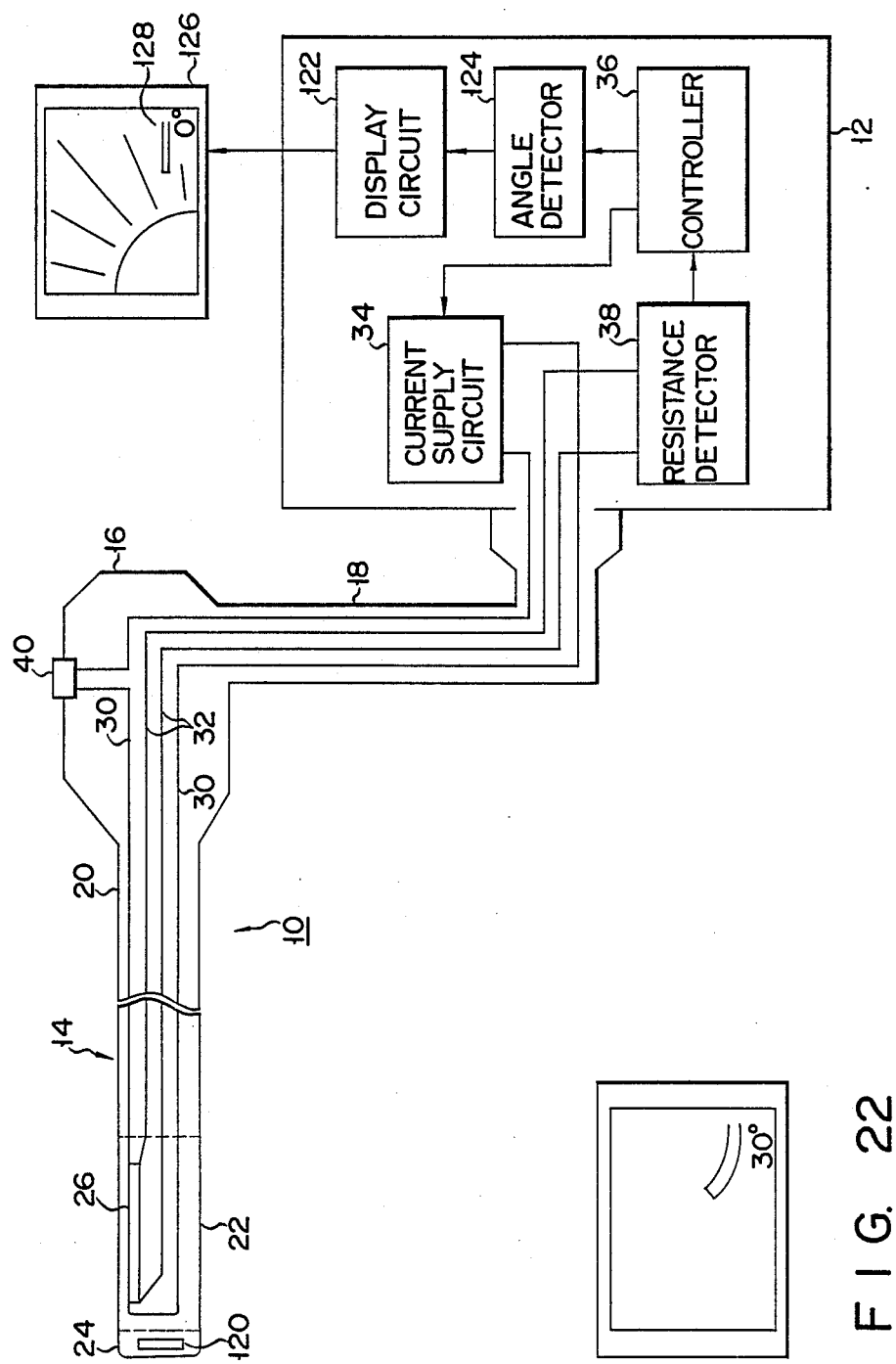
FIG. 21 is a block diagram of an endoscope device according to an eighth embodiment of this invention.
FIG. 22 is a block diagram of a modification of the eighth embodiment.

FIG. 21 is a block diagram of an eighth embodiment. In this embodiment, the construction of the endoscope itself is the same as that in the first embodiment, and SMA 26 is connected to wires 30 and 32. Solid state imaging device 120 for picking up the image of an object is arranged in tip end forming portion 24. An image signal output from solid state imaging device 120 is supplied to display circuit 122 provided in light source device 12 via a signal line (not shown) arranged in inserting section 14 and universal cord section 18. An output from resistance detector 38 connected to SMA 26 via wires 32 is supplied to controller 36. Controller 36 is connected to angle detector 124 which derives out a bending angle of bending member 22 from the resistance of SMA 26. Further, angle detector 124 is connected to display circuit 122 which synthesize the image signal and a detection signal from angle detector 124 and displays the synthesized signal on monitor device 126. In other words, bending degree display portion 128 is assigned on right-lower corner portion of the monitor screen, the bending angle is displayed in figures on bending degree display portion 128, and the image of bending degree display portion 128 is bent according to the shape of bending member 22.

Current supply circuit 34 is capable of controlling the amount of current supplied to SMA 26 to set the resistance of SMA 26 to a value corresponding to a desired bending angle and then keeps the resistance at the desired value.

SMA 26 is set in the martensite phase at a normal temperature prior to the current supply, and it is kept in a straight form. After switch 40 is turned on and current (current pulse) is supplied to SMA 26, SMA 26 is heated and gradually transferred to the austenite phase. This causes the shape of SMA 26 to be changed from the straight form to the memorized bent shape. In this case, resistance detector 38 detects variation in the resistance of SMA 26 caused by the phase-change to the austenite phase during the off period of the current pulse. Also, in this embodiment, since the resistance of SMA 26 is detected by use of the exclusive wire (wire 32) other than heating current supplying wire 30, the resistance of SMA 26 can be correctly detected without receiving any influence by variation in the resistance due to the heated current supplying wire. The detected resistance is converted to a bending degree, and the displayed figures indicating the bending degree displayed on bending degree display portion 128 are changed according to the newly derived bending degree and at the same time the image of display portion 128 is bent accordingly.

FIG. 22 shows a display example of bending degree display portion 128 in the case where the bending angle of SMA 26 is 30°.

Figure 23:
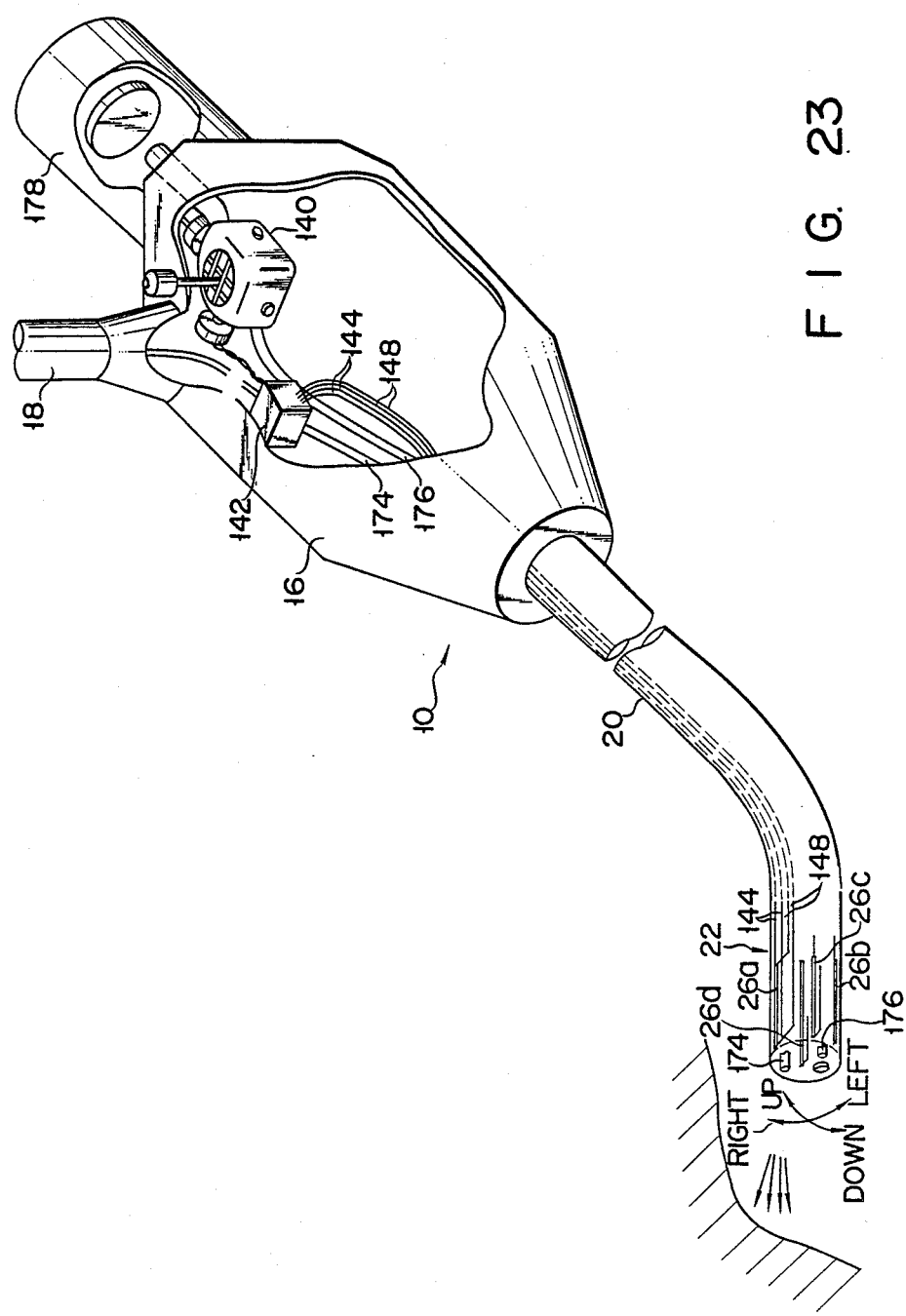
FIG. 23 is a block diagram of an endoscope device according to a ninth embodiment of this invention.

FIG. 23 is a block diagram of a ninth embodiment. Bending degree specifying section 140 is provided in operating section 16 of endoscope 10, and supplies signals specifying the bending degrees in four directions or vertical and horizontal directions to signal processing circuit 142. Outputs from signal processing circuit 142 are supplied, via current supplying wires 144, to SMAs 26a, 26b, 26c and 26d provided in bending member 22 to perform bending operations in the upper, lower, right and left directions. SMAs 26a to 26d are energized by currents corresponding to the bending degree and directions specified by bending degree specifying section 140, thus bending member 22 in any of the upper, lower, right and left directions. The resistances of SMAs 26a to 26d are detected by means of a resistance detector provided in signal processing circuit 142 via wires 148 for resistance detection.

Figure 24:
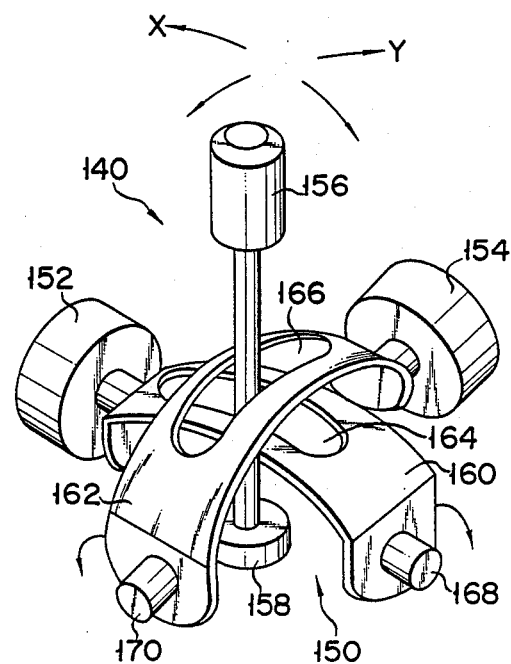
FIG. 24 is a block diagram of a bending command means in the ninth embodiment.

As shown in FIG. 24, bending degree specifying section 140 has joy stick 150 and two potentiometers 152 and 154. Operation lever 156 of joy stick 150 is fixed at supporting point 158, and is formed to extend through long and narrow openings 164 and 166 which are respectively formed in X-axis rotation frame 160 for specifying the bending angle of bending member 22 in the horizontal direction or the angle with respect to the X-axis and in Y-axis rotation frame 162 for specifying the bending angle of bending member 22 in the vertical direction or the angle with respect to the Y-axis. Rotation frames 160 and 162 are disposed to intersect each other at right angles, and are freely rotated by operation of operation lever 156 with shafts 168 and 170 as the respective rotation centers. Potentiometers 152 and 154 are coaxially mounted on shafts 168 and 170, respectively, and generate voltage signals corresponding to the rotation amounts of rotation frames 160 and 162.

Signal processing circuit 142 receives signals corresponding to the bending degrees in the vertical and horizontal directions and generated from potentiometers 152 and 154, and supplies an output signal to drive four SMAs 26a to 26d.

Light guide fiber 174 and image guide fiber 176 are arranged in endoscope 10. Light guide fiber 174 has a light emitting end disposed in tip end forming portion 24 of inserting section 20, and transmits illumination light from the light source device to the light emitting end through the universal cord, operating section and inserting section. Image guide fiber 176 has a light receiving end arranged in tip end forming portion 24, and transmits the optical image of an object to eyepiece 178 through the inserting section and operating section.

In this embodiment, in order to bend the tip end portion of the endoscope, operating lever 156 of joy stick 150 provided in operating section 16 is bent in a corresponding direction. The operation of lever 156 causes X-axis rotation frame 160 and Y-axis rotation frame 162 to rotate around respective shafts 168 and 170. Rotation of the shafts causes output voltages of potentiometers 152 and 154 to change, and signal processing circuit 142 derives out the horizontal bending direction and the bending degree.

FIG. 25 is a block diagram of a tenth embodiment. Two SMAs 26 are provided in bending member 22, and terminal elements 200 are disposed near respective SMAs 26. Each of SMAs 26 is series-connected with a corresponding one of terminal elements 200, and both ends of each series circuit of SMA 26 and terminal element 200 are connected to current supply circuit 34 via wires 30. Further, both ends of SMA 26 are connected to resistance detector 38 via wires 32. Current supply circuit 34, resistance detector 38 and energization controller 12 are arranged in light source device 12.

Each SMA 26 includes deformable or displacement portion 26A which is deformed into a memorized shape by passing current therethrough, positioning portion 26B for setting the positional relation between the entire portion of SMA 26 and terminal element 200, and current supply interrupting portion 26C for interrupting current supply to prevent SMA 26 from being excessively heated. Positioning portion 26B is fixed on a housing (not shown), for example. Deformable portion 26A and current supply interrupting portion 26C are subjected to different heat treatments to have different shape-restoring temperatures.

Figure 27A:
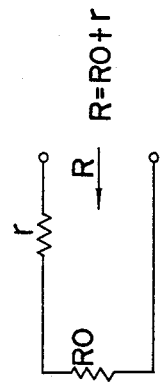
FIGS. 27A to 27C are equivalent circuit diagrams of FIGS. 26A to 26C.
Figure 27B:
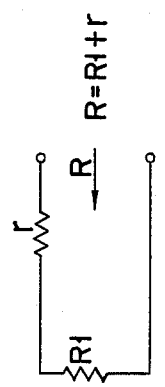
Figure 27C:
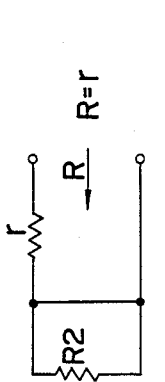
Figure 26A:
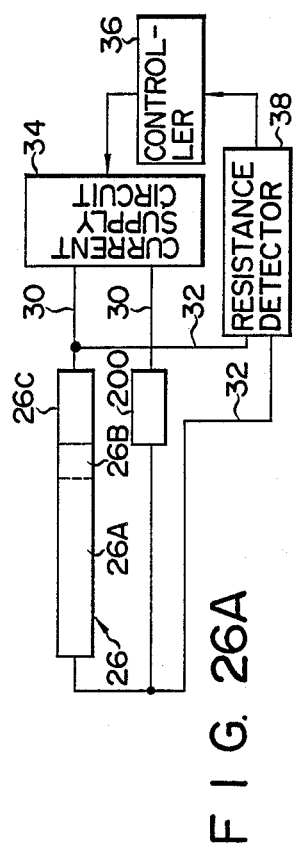
FIGS. 26A to 26C are diagrams showing the displacement of SMA in the tenth embodiment.
Figure 26B:
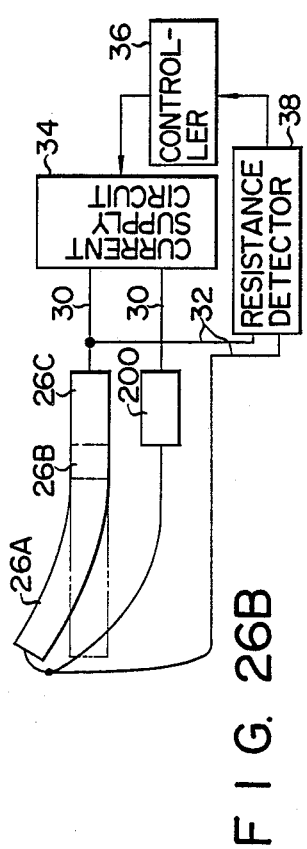
Figure 26C:
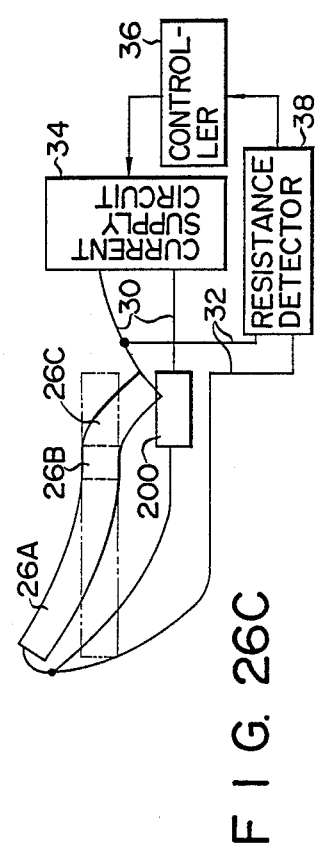

FIGS. 26A, 26B and 26C show SMA 26 and the peripheral parts thereof in the case where temperature T is in the range of $T<T_0$, $T_0 \leq T \leq T_1$, and $T_1 < T$. Temperatures T0 and T1 are upper and lower limits of the temperature range in which SMA 26 can correctly operate. FIGS. 27A, 27B and 27C are equivalent circuits of the circuits shown in FIGS. 26A, 26B and 26C, respectively. R0, R1 and R2 denote the resistances of SMA 26, and r denotes the resistance of wire 30.

Figure 28:
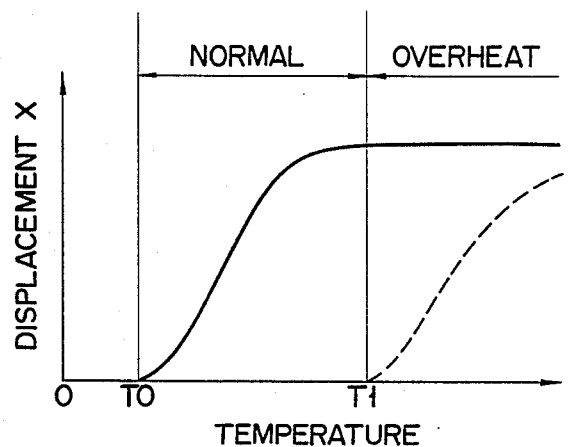
FIG. 28 is a diagram showing the characteristics of SMA in the tenth embodiment.

FIG. 28 shows the relation between the displacement of SMA 26 and temperature, and deformable portion 26A and current supply interrupting portion 26C have characteristics shown by solid and broken lines, respectively. Temperature range of T0 to T1 is the normal operation range, and the temperature region above T1 is an overheat range. Deformable portion 26A starts to be bent or displaced when the temperature exceeds T0, and restored to the memorized shape when temperature T1 is reached. Current supply interrupting portion 26C starts to be bent when the temperature exceeds T1.

Now, the operation of the tenth embodiment is explained.

When current is passed via SMA 26, it is heated by Joule heat. When the temperature exceeds T0, deformable portion 26A starts to be deformed and is bent as shown in FIG. 26B. When the temperature is in the range of T0 to T1, deformable portion 26A is displaced by an amount corresponding to the amount of current supplied by current supply circuit 34. Therefore, the amount of displacement of SMA 26 can be controlled by the amount of current.

Since, in this case, wire 30 is heated as well as SMA 26, the resistance thereof changes with variation in temperature. However, since no heating current is supplied to wire 32, the resistance thereof does not change. In this embodiment, resistance detector 38 detects the resistance of SMA 26 by use of wire 32, the resistance of SMA 26 can be precisely detected without receiving any influence by variation in the resistance of wire 30. Resistance detector 38 detects the resistance of SMA 26 which changes with temperature, derives out the amount of displacement of deformable portion 26A from the detected resistance, and controls the amount of current supplied from current supply controller 36 so as to attain a desired amount of displacement. Current supply circuit 34 supplies a current pulse to SMA 26 at a regular interval, and controls the amount of current by changing the duty ratio of the current pulse.

However, in the case where a heavy load is used, it is necessary to increase the amount of current required for obtaining a desired amount of displacement. At this time, temperature T of SMA 26 will exceed upper limit T1 of the normal operation range and is set in the overheat range ($T_1 < T$). If current is continuously supplied, the shape memory function of SMA 26 is deteriorated or lost and peripheral parts will be damaged.

In this embodiment, when the temperature exceeds T1, current supply interrupting portion 26C is deformed as shown in FIG. 26C, making current supply interrupting portion 26C in contact with terminal element 200. Therefore, both ends of SMA 26 are directly connected as shown in FIG. 27C, interrupting the current supply. As a result, the temperature of SMA 26 is lowered and it is prevented from being overheated. When the temperature is lowered to T1, current supply interrupting portion 26C is separated from terminal element 200 to start the current supply.

Now, modifications of the tenth embodiment are explained.

Figure 29:
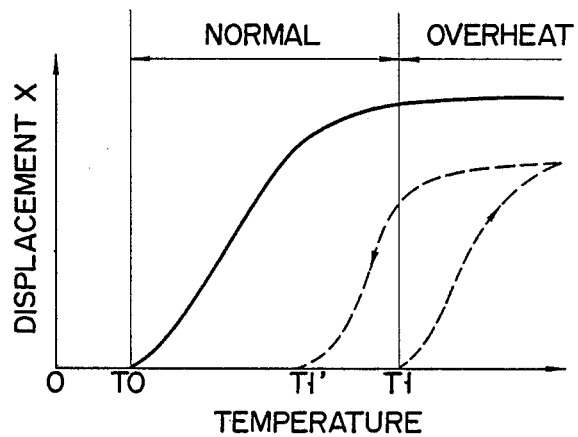
FIG. 29 is a diagram showing the characteristics of SMA in a first modification of the tenth embodiment.

In the first modification, SMA 26 having the characteristics as shown in FIG. 29 is used. The characteristic of deformable portion 26A shown by the solid line is the same as that of the tenth embodiment, but current supply interrupting portion 26C is subjected to a heat treatment so as to have large hysteresis characteristics as shown by the broken lines. Temperature at which current supply interrupting portion 26C starts the shape restoring operation is set at T1 in the same manner as in the tenth embodiment, but temperature at which the displacement is completely eliminated is set at T1' which is lower than T1.

In the first modification, when the temperature exceeds T1, current supply interrupting portion 26C is deformed and set in contact with terminal element 200 so as to interrupt the current supply as in the tenth embodiment. Then, the current supply is kept interrupted until the temperature is sufficiently lowered and becomes below T1' which is within the normal operation range. In the tenth embodiment, since current supply is interrupted when the temperature exceeds T1 and the current supply is started immediately after the temperature becomes below T1, the temperature may oscillate near T1. However, in the first modification, current supply interrupting portion 26C has a large hysteresis, and therefore if current supply is interrupted, the current supply is not started again until the temperature becomes lower than the temperature at which the current supply is interrupted. Thus, the temperature of the actuator can be sufficiently lowered.

FIGS. 30A, 30B and 30C are block diagrams of a second modification showing SMA 26 and other parts in the case where temperature T is set in the range of T<T0, T0≦T≦T1 and T1<T. In the tenth embodiment, deformable portion 26A and current supply interrupting portion 26C are subjected to different heat treatments, but in the second modification, they are formed of SMAs which are subjected to the same heat treatment to have the same characteristics. In this example, distance l between current supply interrupting portion 26C and terminal element 200 is so determined that current supply interrupting portion 26C can be made in contact with terminal element 200 when the temperature becomes higher than T1.

In the second modification, the manufacturing process of SMA 26 can be simplified.

FIG. 31 is a block diagram of a third modification. In this example, a series circuit of SMA 26 and terminal element 200 is connected to current supply circuit 34 via wire 30 and to resistance detector 38 via wire 32.

In the third modification, resistance detector 38 detects the sum of the resistances of SMA 26 and wire 30. As shown in FIG. 27C, current supply controller 36 determines that the temperature is in the overheat range when resultant resistance R becomes equal to resistance r of wire 30, and interrupts the current supply. Current supply controller 36 keeps the interruption of current supply for a preset period of time. When the period of interruption time is set to a desired time, the same effect as in the first modification in which SMA having a large hysteresis is used can be attained. Thus, in the third modification, a double protection against the overheat is taken to attain highly reliable safety.

FIG. 32 is a block diagram of a fourth modification in which both ends of SMA 26 are connected to current supply circuit 34 via wires 30. Terminal element 200 is not connected between wires 30, but is arranged separately from SMA 26 and connected to wire 30 and to resistance detector 38 via wire 32.

In the fourth modification, resistance detector 38 determines that the temperature is in the overheat range when current supply interrupting portion 26C is set in contact with terminal 200, and current supply controller 36 interrupts the current supply effected by current supply circuit 34.

FIG. 33 is a block diagram of a fifth modification. In contrast with the fourth modification, in the fifth modification, SMA 26 is so arranged that current supply interrupting portion 26C can be set in contact with terminal element 200 in the normal temperature range as shown by broken lines. When the temperature is set in the overheat range, current supply interrupting portion 26C is separated from terminal element 200 as shown by solid lines.

Resistance detector 38 determines that the temperature is in the overheat range when current supply interrupting portion 26C is separated from terminal element 200, and current supply controller 36 interrupts the current supply effected by current supply circuit 34.

Figure 34A:
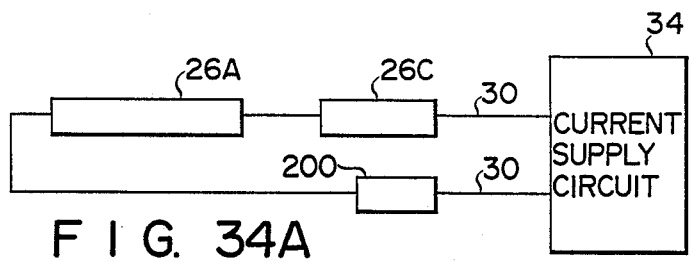
FIGS. 34A to 34C are diagrams showing displacements of SMA of a sixth modification of the tenth embodiment.
Figure 34B:
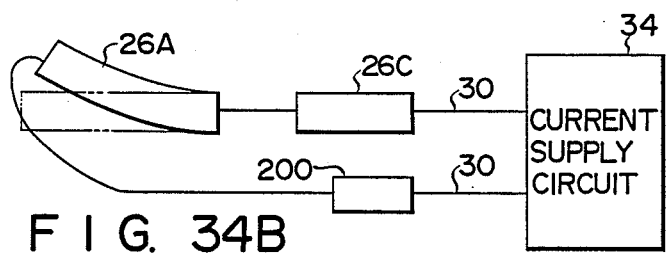
Figure 34C:
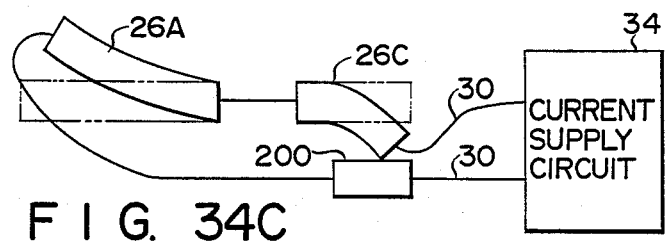

FIGS. 34A, 34B and 34C are block diagrams of a sixth modification in which deformable portion 26A and current supply interrupting portion 26C in the tenth embodiment are formed of different SMAs and portions 26A and 26C are respectively fixed to the housing so that positioning portion 26B can be omitted. Further, in this modification, resistance detector 38 and current supply controller 36 are omitted.

In this modification, when the temperature is in the overheat range, current supply interrupting portion 26C is deformed and made in contact with terminal element 200 as shown in FIG. 34C. Thus, both ends of SMA 26 are directly connected, and the current supply to SMA 26 is interrupted.

In this modification, it is not necessary to heat-treat both ends of SMA 26 corresponding to deformable portion 26A and current supply interrupting portion 26C at different temperatures, and it is only required to heat-treat two SMAs at different temperatures, making the manufacturing process simple. Further, it is not necessary to control current supply controller 36, making the construction simple.

Figure 35:
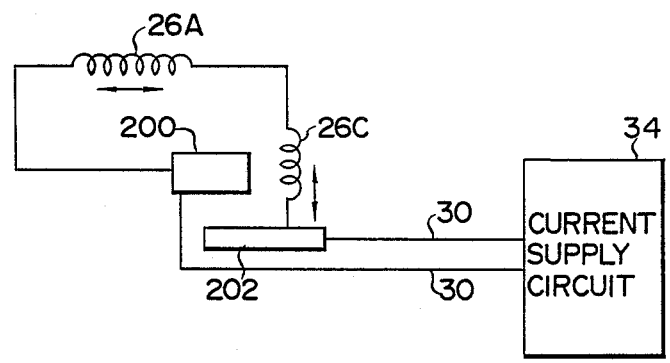
FIG. 35 is a block diagram of a seventh modification of the tenth embodiment.

FIG. 35 is a block diagram of a seventh embodiment in which the SMA in the sixth modification is formed in a spiral form. Deformable portion 26A and current supply interrupting portion 26C are displaced in horizontal and vertical directions as shown by arrows in FIG. 35, and movable contact element 202 to be set in contact with terminal element 200 is connected to the rear end of current supply interrupting portion 26C.

In this modification, when the temperature lies in the overheat range, current supply interrupting portion 26C shrinks and sets movable contact element 202 into contact with terminal element 200. As a result, both ends of SMA 26 are directly connected and the current supply to SMA 26 is interrupted.

In the above modification, since the temperature is detected based on the amount of deformation of the SMA, overheat can be correctly prevented with high reliability. Further, since the shape-restoration temperature of current supply interrupting portion 26C can be set to a given temperature, the temperature at which current supply is interrupted can be freely set.

FIG. 36 is a block diagram of an eighth modification in which temperature sensor 204 such as thermistor is mounted on part of SMA 26 to detect the temperature of SMA 26. Detected temperature is supplied to temperature determination circuit 206 which in turn checks whether or not the temperature is in the normal operation temperature range. If it is detected that the temperature is not in the normal operation temperature range, temperature determination circuit 206 causes current supply controller 36 to interrupt the current supply operation of current supply circuit 34.

As described above, according to this invention, the resistance of SMA can be precisely detected irrespective of variation in the resistance of wires used for passing heating current through the SMA.

Further, even when the resistance detector is provided separately from the main body of the endoscope, the resistance of SMA can be detected irrespective of variation in the resistance of the SMA itself and the length of current supply wires.

What is claimed is:

1. An endoscope device comprising:

an endoscope body including bending means having a shape memory alloy disposed therein; and an external device detachably connected to said endoscope body and including current supply means for supplying current to said shape memory alloy via a current supply wire means to heat said shape memory alloy, means for detecting the resistance of said shape memory alloy, means for controlling said current supply means based on the resistance detected by said detecting means, and said detecting means including means for detecting the resistance of said shape memory alloy by use of a wire means other than said current supply wire means.

2. An endoscope device according to claim 1, in which
said endoscope body includes a conductive wire having the same characteristics as said current supply wire and provided along said shape memory alloy and current supply wire; and
said detecting means comprises:
first detecting means for detecting the resistance of said conductive wire;
second detecting means for detecting the resistances of said current supply wire and shape memory alloy; and
third detecting means for detecting a difference between the resistances detected by said first and second detecting means.

3. An endoscope device according to claim 2, in which said conductive wire is connected to said current supply means.

4. An endoscope device according to claim 1, in which said detecting means comprises:
second shape memory alloy having the same characteristics as said shape memory alloy disposed in said bending means and series-connected to said current supply wire and shape memory alloy; and
means for detecting the resistance of said second shape memory alloy.

5. An endoscope device according to claim 4, in which said second shape memory alloy is connected to said current supply means.

6. An endoscope device according to claim 1, further comprising:
means for converting the detected resistance into the bending degree of said bending means; and
means for displaying the bending degree.

7. An endoscope device according to claim 1, further comprising:
means for detecting the temperature of said shape memory alloy; and
means for interrupting the operation of said current supply means when the temperature is outside a normal operating range.

8. An endoscope device according to claim 1, in which said external device comprises:
a plurality of detecting means provided for respective types of endoscope bodies; and
means for selectively connecting one of said plurality of detecting means to said shape memory alloy.

9. A device according to claim 1, in which said current supply wire means comprises a first wire connecting one end of said shape memory alloy and said current supply means and a second wire connecting the other end of said shape memory alloy and said current supply means, and said wire means other than said current supply wire means comprises a third wire connecting one end of said shape memory alloy and said detecting means and a fourth wire connecting the other end of said shape memory alloy and said detecting means.

10. An endoscope device comprising:
an endoscope body including bending means which is provided at a tip end and has a shape memory alloy disposed therein and means for detecting the resistance of said shape memory alloy; and
an external device detachably connected to said endoscope body and including current supply means for supplying current to said shape memory alloy via a current supply wire means to heat said shape memory alloy and means for controlling said current supply means according to the resistance detected by said detecting means,
said detecting means including means for detecting the resistance of said shape memory alloy by use of a conductive wire means other than said current supply wire means.

11. An endoscope device according to claim 10, in which
said endoscope body includes a conductive wire having the same characteristics as said current supply wire and provided along said shape memory alloy and current supply wire; and
said detecting means comprises:
first detecting means for detecting the resistance of said conductive wire;
second detecting means for detecting the resistances of said current supply wire and shape memory alloy; and
third detecting means for detecting a difference between the resistances detected by said first and second detecting means.

12. An endoscope device according to claim 11, in which said conductive wire is connected to said current supply means.

13. An endoscope device according to claim 10, in which said detecting means comprises:
second shape memory alloy having the same characteristics as said shape memory alloy disposed in said bending means and series-connected to said current supply wire and shape memory alloy; and
means for detecting the resistance of said second shape memory alloy.

14. An endoscope device according to claim 13, in which said second shape memory alloy is provided in a connector section connected to said external device of said endoscope body.

15. An endoscope device according to claim 13, in which said second shape memory alloy is connected to said current supply means.

16. An endoscope device according to claim 10, further comprising:
means for converting the detected resistance into the bending degree of said bending means; and
means for displaying the bending degree.

17. An endoscope device according to claim 10, further comprising:
means for detecting the temperature of said shape memory alloy; and
means for interrupting the operation of said current supply means when the temperature is outside a normal operation range.

18. An endoscope device according to claim 10, in which said detecting means is provided in a connector section connected to said external device of said endoscope body.

19. A device according to claim 10, in which said current supply wire means comprises a first wire connecting one end of said shape memory alloy and said current supply means and a second wire connecting the other end of said shape memory alloy and said current supply means, and said wire means other than said current supply wire means comprises a third wire connecting one end of said shape memory alloy and said detecting means and a fourth wire connecting the other end of said shape memory alloy and said detecting means.

20. An endoscope device comprising:
bending means having a shape memory alloy disposed therein;
current supply means for supplying current to said shape memory alloy via a current supply wire means to heat said shape memory alloy;
means for detecting the resistance of said shape memory-alloy;
means for specifying the bending degree of said bending means;
means for controlling said current supply means based on the detected resistance and the specified bending degree, and
said detecting means including means for detecting the resistance of said shape memory alloy by use of a wire means other than said current supply wire means.

21. An endoscope device according to claim 20, in which
said bending means includes a plurality of shape memory alloys connected in parallel;
said specifying means includes means for specifying a bending direction of said bending means; and
said control means includes means for controlling a current to each of said shape memory alloys according to the specified bending direction.

22. An endoscope device according to claim 21, in which said bending means includes a plurality of series-connected shape memory alloys.

23. A device according to claim 20, in which said current supply wire means comprises a first wire connecting one end of said shape memory alloy and said current supply means and a second wire connecting the other end of said shape memory alloy and said current supply means, and said wire means other than said current supply wire means comprises a third wire connecting one end of said shape memory alloy and said detecting means and a fourth wire connecting the other end of said shape memory alloy and said detecting means.

24. An endoscope device according to claim 21, in which
said endoscope body includes a conductive wire having the same characteristics as said current supply wire and provided along said shape memory alloy and current supply wire; and
said detecting means comprises:
first detecting means for detecting the resistance of said conductive wire;
second detecting means for detecting the resistances of said current supply wire and shape memory alloy; and
third detecting means for detecting a difference between the resistances detected by said first and second detecting means.

25. An endoscope device according to claim 24, in which said conductive wire is connected to said current supply means.

26. An endoscope device according to claim 20, in which said detecting means comprises:
second shape memory alloy having the same characteristics as said shape memory alloy disposed in said bending means and series-connected to said current supply wire and shape memory alloy; and
means for detecting the resistance of said second shape memory alloy.

27. An endoscope device according to claim 26, in which said second shape memory alloy is connected to said current supply means.

28. An endoscope device according to claim 20, further comprising:
means for converting the detected resistance into the bending degree of said bending means; and
means for displaying the bending degree.

29. An endoscope device according to claim 20, further comprising:
means for detecting the temperature of said shape memory alloy; and
means for interrupting the operation of said current supply means when the temperature is outside a normal operation range.

30. An actuator device comprising:
an actuator formed of a shape memory alloy;
current supply means for supplying current to said shape memory alloy via a current supply wire means to heat said shape memory alloy;
means for detecting the resistance of said shape memory alloy;
means for controlling said current supply means based on the resistance detected by said detecting means, and
said detecting means including means for detecting the resistance of said shape memory alloy by use of a wire means other than said current supply wire means.

31. A device according to claim 30, in which said current supply wire means comprises a first wire connecting one end of said shape memory alloy and said current supply means and a second wire connecting the other end of said shape memory alloy and said current supply means, and said wire means other than said current supply wire means comprises a third wire connecting one end of said shape memory alloy and said detecting means and a fourth wire connecting the other end of said shape memory alloy and said detecting means.

32. An actuator device according to claim 30, in which said detecting means comprises:
a conductive wire having the same characteristics as said current supply wire and provided along said shape memory alloy and current supply wire;
first detecting means for detecting the resistance of said conductive wire;
second detecting means for detecting the resistances of said current supply wire and shape memory alloy; and
third detecting means for detecting a difference between the resistances detected by said first and second detecting means.

33. An actuator device according to claim 32, in which said conductive wire is connected to said current supply means.

34. An actuator device according to claim 30, in which said detecting means comprises:
second shape memory alloy having the same characteristics as said shape memory alloy and series-connected to said current supply wire and shape memory alloy; and means for detecting the resistance of said second shape memory alloy.

35. An actuator device according to claim 34, in which said second shape memory alloy is connected to said current supply means.

36. An actuator device according to claim 30, further comprising:
means for converting the detected resistance into the bending degree of said bending means; and
means for displaying the bending degree.

37. An actuator device according to claim 30, further comprising:
means for detecting the temperature of said shape memory alloy; and
means for interrupting the operation of said current supply means when the temperature is outside a normal operation range.

38. A shape memory alloy device comprising:
deformable means including a current supply wire means and a shape memory alloy whose resistance varies when heated;
means for detecting the resistance of said shape memory alloy, and
said detecting means including means for detecting the resistance of said shape memory alloy by use of a wire means other than said current supply wire means.

39. A device according to claim 38, in which said current supply wire means comprises a first wire connecting one end of said shape memory alloy and said current supply means and a second wire connecting the other end of said shape memory alloy and said current supply means, and said wire means other than said current supply wire means comprises a third wire connecting one end of said shape memory alloy and said detecting means and a fourth wire connecting the other end of said shape memory alloy and said detecting means.

40. A shape memory alloy device according to claim 38, in which said detecting means comprises:
a conductive wire having the same characteristics as said current supply wire and provided along said shape memory alloy and current supply wire;
first detecting means for detecting the resistance of said conductive wire;
second detecting means for detecting the resistances of said current supply wire and shape memory alloy; and
third detecting means for detecting a difference between the resistances detected by said first and second detecting means.

41. A shape memory alloy device according to claim 40, in which said conductive wire is connected to said current supply means.

42. A shape memory alloy device according to claim 38, in which said detecting means comprises:
second shape memory alloy having the same characteristics as said shape memory alloy and series-connected to said current supply wire and shape memory alloy; and
means for detecting the resistance of said second shape memory alloy.

43. A shape memory alloy device according to claim 42, in which said second shape memory alloy is connected to said current supply means.

44. A shape memory alloy device according to claim 38, further comprising:
means for converting the detected resistance into the bending degree of said bending means; and
means for displaying the bending degree.

45. A shape memory alloy device according to claim 38, further comprising:
means for detecting the temperature of said shape memory alloy; and
means for interrupting the operation of said current supply means when the temperature is outside a normal operation range.

46. An endoscope comprising:
bending means which is provided at a distal end of the endoscope and has a shape memory alloy disposed therein; and
inserting means having at least current supply wires connected to both ends of the shape memory alloy for supplying a heating current to the shape memory alloy, and other wires connected to both ends of the shape memory alloy for detecting a resistance of the shape memory alloy.

* * * * *

UNITED STATES PATENT AND TRADEMARK OFFICE
CERTIFICATE OF CORRECTION

PATENT NO. : 4,884,557

DATED : December 5, 1989

INVENTOR(S) : SAKAE TAKEHANA ET AL

It is certified that error appears in the above-identified patent and that said Letters Patent is hereby corrected as shown below:

Title page, Item [30], line 7, "Apr. 12," should be -- Apr. 13 --.

Signed and Sealed this

Thirteenth Day of August, 1991

*Attest:*

HARRY F. MANBECK, JR.

*Attesting Officer*     *Commissioner of Patents and Trademarks*